United States Patent [19]

Weir

[11] 3,994,884

[45] Nov. 30, 1976

[54] 3-VINYL-7β-(2,2-DISUBSTITUTED ACETAMIDO)-CEPHALOSPORINS

[75] Inventor: Niall Galbraith Weir, London, England

[73] Assignee: Glaxo Laboratories Limited, Greenford, England

[22] Filed: Feb. 8, 1974

[21] Appl. No.: 440,753

Related U.S. Application Data

[63] Continuation of Ser. No. 108,134, Jan. 20, 1971, abandoned.

[30] Foreign Application Priority Data

June 10, 1970 United Kingdom............... 28194/70
Jan. 12, 1971 United Kingdom................. 3464/70
Jan. 12, 1971 United Kingdom............... 21907/70

[52] U.S. Cl. .............................. 260/243 C; 424/246
[51] Int. Cl.² ........................................ C07D 501/20
[58] Field of Search ................................ 260/243 C

[56] References Cited
UNITED STATES PATENTS
3,769,277  10/1973  Long et al...................... 260/243 C

*Primary Examiner*—Nicholas S. Rizzo
*Attorney, Agent, or Firm*—Bacon & Thomas

[57] ABSTRACT

The invention is concerned with $\Delta^3$-4-carboxy cephalosporin antibiotics possessing a 3-vinyl group and having 2,2-disubstituted acetamido group at the 7-position.

5 Claims, No Drawings

3-VINYL-7β-(2,2-DISUBSTITUTED ACETAMIDO)-CEPHALOSPORINS

This application is a continuation of application Ser. No. 108,134, filed Jan. 20, 1971 and now abandoned.

This invention is concerned with improvements in or relating to antibiotics. In particular, the invention is concerned with a novel group of cephalosporin antibiotics possessing activity against a range of gram positive and gram negative organisms.

The cephalosporin compounds referred to in this specification are generally named with reference to cepham (see J. Amer. Chem. Soc. 1962, 84, 3400). The term "cepham" refers to the basic cepham structure with a single double bond. Where a dotted line bridges the 2-, 3- and 4-positions this indicates that the compound may be a ceph-2-em or ceph-3-em compound.

According to the invention there are provided compounds of the general formula

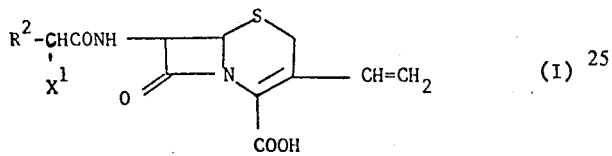

where $R^2$ is an aromatic group, e.g. phenyl or phenyl substituted with halo, hydroxy, lower alkyl, nitro, amino, lower alkanoyl, lower alkoxy or lower alkylmercapto, or a heterocyclic group, (particularly a 5- or 6-membered heterocyclic group containing at least one hetero atom selected from S, N and O, e.g. thien-2-yl or thien-3-yl); $X^1$ is amino, substituted amino (e.g. acylamido), hydroxyl or substituted hydroxyl (e.g. acyloxy); and non-toxic derivatives thereof e.g. base salts (where applicable) and acid addition salts (where applicable) and compounds obtained by reacting a compound of formula where $X^1$ = an amino group with an aldehyde or ketone e.g. acetone or methyl ethyl ketone.

By the term "non-toxic" as applied to the compounds of the invention we mean those derivatives which are physiologically acceptable in the dosage at which they are administered. Such derivatives include salts and esters.

Compounds according to the invention possess antibacterial activity against a range of gram positive and gram negative organisms and are of value in human and veterinary medicine. They may also be of value in the preparation of other 3-substituted cephalosporin compounds.

The compounds of formula (I), or salts thereof, may be used as a mixture of diastereoisomers or in one of the pure diastereoisomeric forms. Of particular interest are the compounds of the formula (I) wherein the acid $R^2CH(X^1)COOH$ is of the D- series. The derivatives of D(−) phenylglycine and the salts of those derivatives are of especial interest.

A particularly important compound of the general formula (II) is 7α-(D-2-amino-2-phenylacetamido)-3-vinylceph-3-em-4-carboxylic acid of the formula:

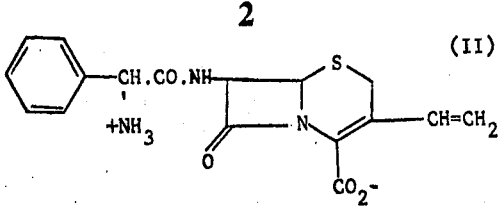

7β-(D-2-Amino-2-phenylacetamido)-3-vinylceph-3-em-4-carboxylic acid is a broad-spectrum antibiotic being active against gram-positive and gram-negative organisms as evidenced by in vitro tests. It is substantially resistant to degradation in vivo as evidenced by animal tests. A particularly significant property of this compound is that, when given by the oral route, it is well absorbed and gives good blood levels. It has an appreciable level of activity on oral administration. It will be appreciated that the property of absorption by the subject after oral administration is highly desirable.

An important series of compounds related to that of formula (II) are compounds of the formula:

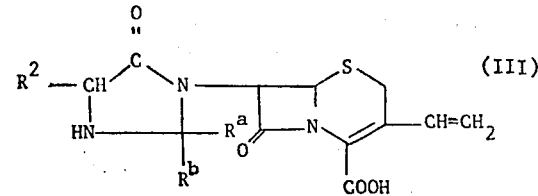

where $R^2$ has the above defined meaning and $R^a$ and $R^b$ which may be the same or different are lower alkyl groups ($C_1 - C_4$), particularly methyl or ethyl, and salts thereof. Such compounds may exist in isomeric forms (cf. J. Org. Chem. 1966, 31, 897).

Salts which may be formed from the compounds according to the invention include (a) inorganic base salts such as alkali metal, e.g. sodium and potassium, alkaline earth e.g. calcium, and organic base salts e.g. procaine and dibenzylethylene diamine salts and (b) acid addition salts e.g. with hydrochloric, hydrobromic, sulphuric, nitric, phosphoric, toluene-p-sulphonic and methanesulphonic acids. The salts may also be in the form of resinates, formed, e.g. with a polystyrene resin containing amino, quaternary amino, or sulphonic acid groups, or a resin containing carboxyl groups, e.g. a polyacrylic acid resin. The resin may if desired be cross-linked, e.g. it may be a copolymer of styrene and divinylbenzene containing the appropriate groups.

Preparation of compounds of general formula (I)

According to a further embodiment of the invention there is provided a process for the preparation of a cephalosporin compound of formula I defined above which comprises (A) reacting a compound of the formula

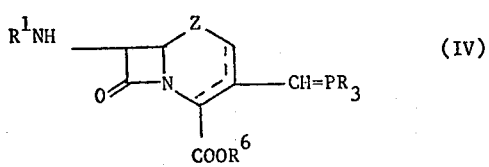

(wherein $R^1$ is a carboxylic acyl group, $R^6$ is hydrogen or a carboxyl-blocking group, Z is $>S$ or $>S \rightarrow O$ ($\alpha$ or $\beta$-) and R is an organic substituting group), or a Zwitterionic form thereof, with formaldehyde. or (B) acylating a compound of the formula

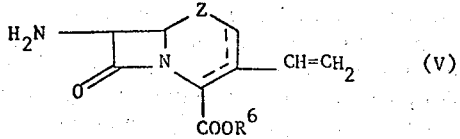

(wherein Z, and $R^6$ have the above defined meanings with an acylating agent corresponding to the acid $R^1COOH$ whereafter, if necessary, any of the following reactions (D) are carried out; (i) conversion of a $\Delta^2$ isomer into the desired $\Delta^3$ isomer, (ii) removal of any groups protecting any amino or carboxyl groups and (iii) reduction of a compound in which Z is $>S \rightarrow O$ to form the desired $Z=>S$ compound.

For the sake of simplicity the group

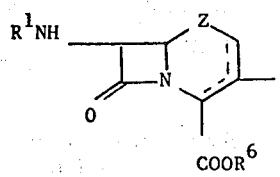

is shown below as Q.

Preparation of compounds of general formula I via 3-phosphoranylidene compounds

This may be effected by a series of reactions which may be depicted as

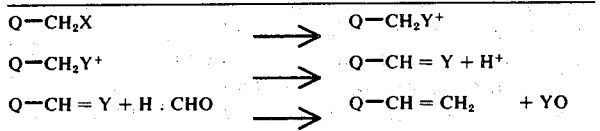

X is halogen i.e. chlorine, bromine or iodine and Y is $PR_3$, R being organic groups. The conversion may also be effected using compounds where Y is $-PO(OR)_2$ although the reaction scheme may be somewhat different.

The R groups may be the same or different and may be alkyl, aralkyl or aryl groups or such groups substituted by, for example, one or more halogen atoms, nitro groups, cyano groups, amino groups, acyl groups, acylamido groups and the like. Examples of R groups include lower alkyl e.g. methyl, ethyl, propyl or butyl; and phenyl or substituted phenyl; and benzyl.

The compounds $QCH_2X$ are 3-halomethylcephalosporins and may be prepared by halogenation of a 7$\beta$-acylamido-3-methylceph-3-em-4-carboxylic acid ester 1$\beta$-oxide followed, if desired, by reduction of the 1$\beta$-oxide group as described in copending Application No. 66,128, filed Aug. 21, 1970 and now abandoned. 3-Halomethylceph-3-em compounds may also be prepared by the method described in Belgian Pat. No. 719,711. The corresponding ceph-2-em compounds may be prepared by the method of Dutch published Patent Application No. 6902013 by reaction of a ceph-2-em-3-methyl compound with N-bromo-succinimide to yield the ceph-2-em-3-bromomethyl compound.

The carboxyl blocking group $R^6$, substituting the 4-carboxyl group, is, preferably, an ester formed with an alcohol or phenol which may readily be split off at a later stage of the reaction.

The group protecting the 4-carboxyl group of formula I may be formed with an alcohol (aliphatic or araliphatic), phenol, silanol, stannanol or acid which may readily be split off at a later stage of the reaction.

Suitable esters thus include compounds containing as 4-ester group, a group selected from the following list which is not intended to be an exhaustive list of possible ester groups i. $-COOCR^aR^bR^c$ wherein at least one of $R^a$, $R^b$ and $R^c$ is an electron-doner e.g. p-methoxyphenyl, 2,2,6-trimethylphenyl, 9-anthryl, methoxy, acetoxy, tetrahydrofur-2-yl, tetrahydropyran-2-yl or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

ii. $-COOCR^aR^bR^c$ wherein at least one of $R^a$, $R^b$ and $R^c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R^a$, $R^b$ and $R^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. $-COOCR^aR^bR^c$ wherein at least two of $R^a$, $R^b$ and $R^c$ are hydrocarbon such as alkyl e.g. methyl or ethyl, or aryl e.g. phenyl and the remaining $R^a$, $R^b$ and $R^c$ group, if there is one, is hydrogen. Suitable esters of this type include, t-butyloxycarbonyl, t-amyloxycarbonyl, diphenylmethoxycarbonyl and triphenylmethoxycarbonyl.

iv. $-COOR^d$ wherein $R^d$ is adamantyl, 2-benzyloxyphenyl, 4-methylthiophenyl or tetrahydropyran-2-yl.

Silyl esters may conveniently be prepared from a halosilane or a silazane of the formula $R_3^4SiX$; $R_2^4SiX$; $R_3^4Si.NR_2^4$; $R_3^4Si.NH.SiR_3^4$; $R_3^4Si.NH.COR^4$; $R_3^4Si.NH.CO.NH.SiR_3^4$; $R^4NH.CO.NR^4.SiR_3^4$; or $R^4C(OSiR_3^4)$: $NSiR_3^4$ where X is a halogen and the various groups $R^4$, which can be the same or different, represent hydrogen atoms or alkyl, e.g. methyl, ethyl, n-propyl, iso-propyl; aryl, e.g. phenyl; or aralkyl e.g. benzyl groups.

Preferred derivatives of silanols are silyl chlorides such as for example trimethylchlorosilane and dimethyldichlorosilane.

The carboxyl groups may be regenerated from an ester by any of the usual methods; for example, acid- and base-catalysed hydrolysis (especially for silyl and stannyl esters) is generally applicable, as well as enzymically-catalysed hydrolysis; however, aqueous mixtures may be poor solvents for these compounds and they may cause isomerizations, rearrangements, side-reactions, and general destruction, so that special methods may be desirable. Five suitable methods of deesterification are:

Reactions with Lewis acids: Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be improved by addition of a nucleophile such as anisole.

Reduction: Suitable systems for effecting reduction are zinc/acetic acid, zinc/formic acid, zinc/lower alcohol, zinc/pyridine, palladised-charcoal and hydrogen, electrolysis, and sodium and liquid ammonia. Attack by nucleophiles: Suitable nucleophiles are those containing a nucleophilic oxygen or sulphur atom for example alcohols, mercaptans and water.

Oxidative methods: for example, which involve the use of hydrogen peroxide and acetic acid. Irradiation.

Preparation of phosphonium compounds

The phosphonium compounds $OCH_2Y^+$ may be prepared by reaction of the corresponding 3-halomethyl compound, preferably the 3-bromo- or 3-iodomethyl ceph-3 or 2-em compound, with a phosphorus-containing nucleophile such as a trivalent phosphorus nucleophile e.g. a phosphine, phosphorus acid or derivative thereof.

The reaction may be carried out in a solvent, preferably an inert organic solvent, since this will facilitate working and, if it is found to be necessary to heat the reaction mixture, the presence of a solvent serves to prevent undesired decomposition during heating. Reactions with 3-bromomethyl and 3-iodomethyl compounds proceed readily at normal temperatures although it may be found to be more efficient to work at elevated temperatures. With 3-chloromethyl compounds heating is usually necessary in order to ensure that the reaction times are practical for normal operating criteria. The reaction may be facilitated by the presence of small amounts (e.g. one equivalent or less) of alkali metal bromides or iodides e.g. sodium bromide or sodium iodide.

Suitable inert solvents include acyclic ethers, e.g. diethyl ether, cyclic ethers e.g. dioxan or tetrahydrofuran; esters e.g. ethyl acetate; hydrocarbons e.g. benzene; halogenated hydrocarbons e.g. methylene chloride; dimethylsulphoxide; amides e.g. dimethylformamide, dimethylacetamide, and hexamethylphosphoramide and the like.

The phosphorus compounds thus obtained are novel compounds and the invention thus provides novel ceph-3 or 2-em compounds having the group $-CH_2Y$ at the 3-position wherein Y is $-P^+R_3$ or $-PO(OR)_2$ and the R groups are organic substituting groups (which may be the same or different). The novel compounds may be defined by the following formula:

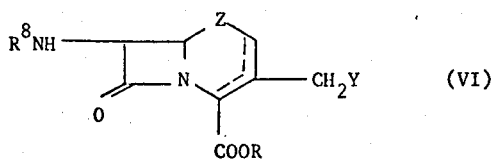

wherein $R^8$ is a hydrogen atom or a carboxylic acyl group $R^1$; $R^6$ is a hydrogen atom or an esterifying group; Z is >S, or >SO and Y has the above defined meaning. When Y is a $P^+R_3$ group, the group at the 4-position may be $COO^-$; compounds of this type may cyclise to form compounds containing pentacovalent phosphorus and they also form salts with strong acids e.g. nitric acid trifluoroacetic acid and/or hydrochloric acid.

Preparation of phosphoranylidene compounds

The phosphonium compounds according to the invention may be converted into the corresponding phosphoranylidene compounds by abstraction of an acidic proton (e.g. from the exocyclic methylene group at the 3-position), the conversion being depicted by the following equation:

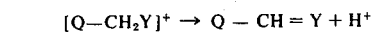

wherein Q has the above-defined meaning.

Formation of the phosphoranylidene compound may be achieved by reacting the phosphonium compound with a base, preferably one stronger than the conjugate base of the phosphonium compound. Suitable bases include alkali metal and alkaline earth metal hydroxides, carbonates and hydrogen carbonates e.g. sodium hydroxide or sodium hydrogen carbonate; disodium hydrogen phosphate; and hydrides e.g. sodium hydride. Other bases which may be used to generate phosphoranylidene compounds include phosphoranylidenes more basic than the phosphoranylidene compound being produced; the conjugate bases of dimethylsulphoxide, dimethylacetamide and dimethylformamide; tertiary nitrogen bases e.g. pyridine or trialkylamines such as triethylamine; the sodio or lithio derivatives of hexamethyldisilazane, onium and alkali metal alkoxides and fluorides; and alkylene oxides in the presence of halide ion e.g. ethylene oxide or propylene oxide in the presence of, for example, bromide ion.

The use of a base at this stage in conjunction with a ceph-2-em compound may convert the cephalosporin compound to a ceph-3-em compound. This enables a convenient isomerisation to be simultaneously effected.

Formation of the phosphoranylidene compound is generally accompanied by a deepening or generation of colour, for example when starting from a solution of an onium compound the solution yellows or reddens as the phosphoranylidene compound is formed, and a strong $\lambda_{max}$ appears at 388 nm., with dwindling of a weaker band at 275 nm, associated with the onium salt. Compounds with phenyl-phosphorus bonds give rise to a peak in their infrared absorption at about 1450 cm.$^{-1}$.

The phosphoranylidene compounds are novel compounds and constitute a further feature of the invention.

The phosphoranylidene compounds may be coupled with formaldehyde to yield the compounds of general formula (I).

It is not necessary to isolate the phosphoranylidene compound in order to carry out the coupling reaction with formaldehyde The phosphoranylidene compound may be formed in situ from a phosphonium compound and a base as described above and coupled in situ with the desired carbonyl compound.

The coupling reaction may be catalysed by a weak organic acid such as benzoic acid.

The reaction with formaldehyde may be carried out by vigorously stirring the components together, e.g. at a temperature of from $-30°$ to $+100°$ C. When the reaction is effected at a temperature at which one or more reactants may volatilise a closed system may be used. The reaction may be effected in an inert or relatively inert solvent, for example, a halogenated hydrocarbon, e.g. methylene chloride; a hydrocarbon e.g. benzene; an acyclic or cyclic ether e.g. diethyl ether, tetrahydrofuran or dioxan; dimethylsulphoxide; an amide e.g. dimethylformamide or dimethylacetamide or hexamethylphosphoramide. The coarse of the reaction may be followed by observing the reduction in colour of the phosphoranylidene compound or the decrease in the $\lambda_{max}$ at 388 nm.

N-Deacylation

The product of (A) may be N-deacylated to yield the corresponding 7β-amino compound.

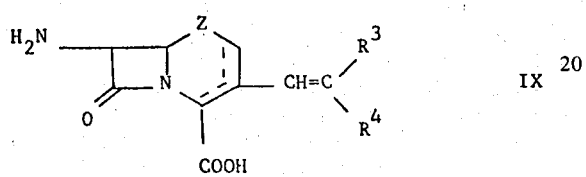

(wherein $R^3$, $R^4$ and Z have the above defined meanings) or a derivative (e.g. ester, salt or salt of ester) thereof. Acid addition salts e.g. with nitric acid or a hydrocarbyl sulphonic acid, may be formed with the free 4-COOH compound or ester thereof. Examples of hydrocarbyl sulphonic acids include alkylbenzene sulphonic acids, e.g. p-toluene sulphonic acid, and lower alkane sulphonic acids, e.g. methane sulphonic acid.

Suitable methods of N-deacylating cephalosporin derivatives having 7β-acylamido groups are described in British Pat. Nos. 1,041,985 and 1,119,806; Belgian Pat. No. 719,712 and in South African patent specification Nos. 68/5048 and 68/5327. Another method of N-deacylation which may be used is acid catalysis. For example, N-deformylation of a 7β-formamido group may be effected with a mineral acid at a temperature of minus 15° to +100° C, preferably +15 to 40° C. N-deformylation may be effected with the aid of a Lewis acid in a lower alkanol, preferably under substantially anhydrous conditions.

C. Acylation

Acylation of a compound of formula (IX) (or ester, salt or salt-ester thereof), may be effected with any convenient acylation agent such as for example, an acid halide (e.g. chloride or bromide), an anhydride or mixed anhydride, e.g. with pivalic acid or formed with a haloformate, e.g. a lower alkylhaloformate, or an active ester or azido; alternatively, the acid itself can be used, together with an esterifying agent, e.g. carbonyldiimidazole or a carbodiimide such as N,N'-diethyl-, dipropyl-, or -diisopropylcarbodiimide, or preferably N,N'-dicyclohexylcarbodiimide Acylation with an acid halide may be effected in the presence of an acid binding agent, e.g. a tertiary amine such as triethylamine, dimethylformamide, dimethylaniline; an inorganic base such as calcium carbonate or sodium bicarbonate; or an oxirane which binds hydrogen halide liberated in the acylation reaction. The oxirane is preferably a lower-1,2-alkylene oxide e.g. ethylene oxide or propylene oxide.

According to a preferred embodiment of the process according to the invention there is provided a process for the preparation of compounds of the formula

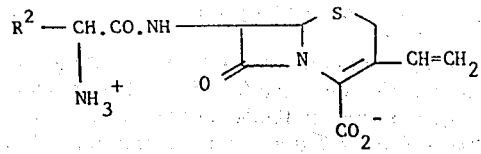

wherein $R^2$ has the above defined meaning, which comprises acylating a compound of the formula

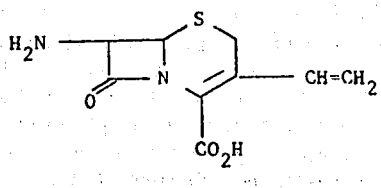

(or an ester, salt or salt-ester thereof) with a compound of the formula

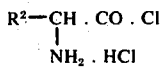

in the presence of an acid-binding agent.

Protection of amino groups.

When the 7β-acylamido group contains an amino group it will be necessary to protect this during the various reaction stages. The protecting group is conveniently one which can be removed by hydrolysis without affecting the rest of the molecule, especially the lactam and 7β-amido linkages. The amine protecting group and the esterifying group at the 4-COOH position can be removed using the same reagent. An advantageous procedure is to remove both groups at the last stage in the sequence. Protected amine groups include urethane, arylmethyl (e.g. trityl) amino, arylmethyleneamino, sulphemylamino or enamine types. Such groups can in general be removed by one or more reagents selected from dilute mineral acids e.g. dilute hydrochloric acid, concentrated organic acids, e.g. concentrated acetic acid, trifluoroacetic acid, and liquid hydrogen bromide at very low temperature, e.g. −80° C. A convenient protecting group is the t-butoxycarbonyl group, which is readily removed by hydrolysis with dilute mineral acid, e.g. dilute hydrochloric acid, or preferably with a strong acid (e.g. formic acid, trifluoroacetic acid or liguid HF) e.g. at a temperature of 0°–40° C., preferably at room temperature (15°–25° C). Another convenient protecting group is the 2,2,2-trichloroethoxycarbonyl group which may be split off by an agent such as zinc/acetic acid, zinc/formic acid, zinc/lower alcohols or zinc/pyridine. The $NH_2$ group may also be protected as $NH_3+$ by using the amino acid halide as its hydrohalide under conditions in which the amino group remains protonated.

Typical protecting groups and their methods of removal are illustrated in the following table:

| Type | Example | Usual Name and Analogues etc. | Usual Method of Removal |
|---|---|---|---|
| Urethane | 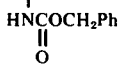 HNCOCH₂Ph ‖ O | Benzyloxycarbonyl, p-Methoxy | HBr/AcOH (Neat) CF₃COOH (Neat) Liq. HBr at −80° C |
| Urethane | HNCOC(CH₃)₃ ‖ O | t-Butoxycarbonyl | Dil. acid (HCl) CF₃COOH (Neat) |
| Urethane | HNCOCHPh₂ ‖ O | Diphenylmethoxycarbonyl | CF₃COOH (Neat) Dil. HCl etc. |
| Urethane | HNCO—(1-adamantyl) ‖ O | 1-Adamantyloxycarbonyl | Dil. HCl |
| Arylmethyl | HNCPh₃ | Trityl | AcOH + H₂O Dil. HCl |
| Sulphenyl | 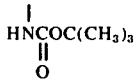 | o-Nitrophenylsulphenyl. p-nitro- | Dil. HCl NaI or Na₂S₂O₃ pH 2–4 |
| Enamine | 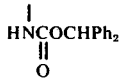 | β-Dicarbonyl R=OEt Ethyl acetoacetate R=CH₃ Acetylacetone R=Ph Benzoylacetone R=OMe Methyl acetoacetate R=C₂H₅ Propionylacetone and many other β-diketones | Acid labile in varying degree Dil-AcOH or HCl etc. |
| Arylmethy- lene | 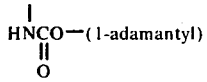 | Anil (similar to β-dicarbonyl) from Salicylaldehyde 5-chlorosalicylaldehyde 3,5-dichlorosalicylaldehyde 2-hydroxy-1-naphthaldehyde 3-hydroxy-pyridine-4-aldehyde | Dil. HCl Formic acid |
| Onium | NH₃⁺ | | Base |
| Urethane | HN . CO . OCH₂CCl₃ | β,β,β-trichloroethoxy- carbonyl | Reducing agents e.g. Zn/acetic acid |

D. Subsequent reactions.

Where the resultant compound contains a sulphinyl group at the 1-position this may be reduced by any convenient means. This may, for example, solvent effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible slvent e.g. acetic acid tetrahydrofuran, dioxan, dimethylformamide or dimethylacetamide. The reaction may be effected at a temperature of −20° to +50° C.

Alternatively, reduction of the 1-sulphinyl group may be effected by phosphorus trichloride or tribromide in solvents such as methylene chloride, dimethylformamide or tetrahydrofuran, preferably at a temperature of −20 ° C to+50° C.

Where the resultant compound is a ceph-2-em compound, the desired ceph-3-em compound may be obtained by treatment of the former with a base e.g. a base of the type used in the preparation of the phosphoranylidene compounds.

Removal of any groups protecting any amino or carboxyl groups may be effected as desired above.

Administration

The compounds according to the invention may be formulated for administration in any convenient way, by analogy with other antibiotics and the invention therefore includes within its scope a pharmaceutical composition comprising a compound of formula (I) or a non-toxic derivative e.g. salt thereof (as herein defined) adapted for use in human or veterinary medicine. Such compositions may be presented for use in conventional manner with the aid of any necessary pharmaceutical carriers or excipients.

The compositions are preferably presented in a form suitable for absorption by the gastro-intestinal tract.

Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example, lecithin, sorbitan mono-oleate or acacia; non-aqueous vehicles which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g. cocoa butter or other glyceride.

Compositions for injection may be presented in unit dose form in ampoules, or in multidose containers with an added preservative. The compositions may take such forms as suspensions, solutions, emulsions in oily or aqueous vehicles, and may contain formulatory agents such as suspending, stabilizing and/or dispersing agents. Alternatively the active ingredients may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders etc.

For veterinary medicine the composition may, for example, be formulated as an intramammary preparation in either long acting or quick-release bases.

The compositions may contain from 0.1% upwards, e.g. 10–99%, preferably from 10–60% of the active material, depending on the method of administration. Where the compositions comprise dosage units, each unit will preferably contain 50–500mg. of the active ingredient. The dosage as employed for adult human treatment will preferably range from 100–300 mg. for instance 1500 mg. per day, depending on the route and frequency of administration.

The compounds according to the invention may be administered in combination with other therapeutic agents such as antibiotics, for example, other cephalosporins, the penicillins or tetracyclines.

In order that the invention may be well understood the following Examples are given by way of illustration only.

In the Examples, unless otherwise stated

1. Ultra-violet (uv) spectra were measured on solutions in ethanol.

2. Infra-red (ir) spectra were measured on mulls in Nujol.

3. Optical rotations were determined at 19 to 30° at concentrations in the range 0.5 to 1.5% as solutions in dimethylsulphoxide. Where other solvents were used the same concentration range applied.

4. Solutions were dried over anhydrous magnesium sulphate.

5. All grades of Kieselgel were supplied by Merck AG Darmstadt, Germany.

6. Proton magnetic resonance (PMR) spectra were determined at 60 or 100 MHz. The signs of the coupling constants (J) are not assigned. Signals are assigned as singlets ($s$) doublets ($d$), double doublets ($dd$), triplets ($t$), quartets($q$), double quartets ($dq$), AB-quartets (AB-$q$), quintets ($qu$) and multiplets ($m$)

System A descending n-propanol:water = 7:3, on Whatman No. 1 Paper at room temperature.

System B is n-butanol:ethanol:water = 4:1:5, equilibrated at room temperature, the upper phase being used as developer in descending manner, in equilibrium with lower phase, on Whatman 3MM paper buffered to pH 6 with 0.05M sodium dihydrogen phosphate.

System C is ethyl acetate: n-butanol. 0.1M-sodium acetate pH 5 = 8:1:8, equilibrated at 38° C, the upper phase being used as developer in descending manner, in equilibrium with lower phase at 38°, on No. 1 Whatman paper buffered to pH 5 with 0.1M sodium acetate.

Light petroleum was the fraction, b.p. 40° to 60°. Methylene chloride was dried on Woelm Grade I basic alumina. Thin-layer chromatography was carried out upwards on Merck silica plates developed with benzene:ethyl acetate = 4:1, or in these conditions.

System D Merck GF$_{254+366}$ plates, with the upper phase of Solvent Mixture B for development.

System E On the plates of System D, with benzene:ethyl acetate = 5:1 for development. Unless otherwise stated R$_F$ values are using System E.

System F As System E, but with benzene:ethyl acetate = 1:1 as solvent.

These abbreviations are used for the appearances of the spots: $s$, strong; $m$, medium; $f$, faint; $v$, very.

As far as possible, analytical values for solvates were confirmed by the inspection for the appropriate features in the spectra.

R$_P$ represents the R$_F$ value divided by that of 3-acetoxymethyl-7β-(phenylacetamido) ceph-3-em-4-carboxylic acid.

R$_T$ represents the R$_F$ value divided by that of 3-acetoxymethyl-7β-(2-thienylacetamido)ceph-3-em-4-carboxylic acid.

The conditions for electrophoresis are those described by Cocker et al., *J. Chem. Soc.* 1965, 5015.

The Examples are divided into the following sections:

A Preparation of cephalosporins having a vinyl group at the 3-position via phosphoranylidene cephalosporin compounds.

i. Preparation of compounds of the 3-CH$_2$Y type.

ii. Preparation of compounds of the 3-CH=Y type from compounds of the 3-CH$_2$Y type.

iii. Preparation of vinyls from compounds of the 3-CH=Y type.

Section A (i)

EXAMPLE 1

[4-Diphenylmethoxycarbonyl-7β-(2-thienylacetamido)ceph-3-em-3-ylmethyl]-triphenylphosphonium iodide A solution of diphenylmethyl 3-iodomethyl-7β-(2-thienylacetamido)ceph-3-em-4-carboxylate (30 g.,) Rf 0.6 in ethyl acetate (500 ml.) was stirred in the dark at room temperature and treated, over 45 minutes, with a solution of triphenylphosphine (24.9 g., ca. 2 equivs.) in ethyl acetate (150 ml.). The mixture was stirred for a further 60 minutes at 0°, and the precipitated solid collected by filtration. The solid was washed with ethyl acetate and dried in vacuo to give the phosphonium iodide (31.7 g., 74.5%),Rf 0.0, m.p. 142°–146° (decomp.), $[\alpha]_D + 10°$ (tetrahydrofuran), $\lambda_{max}$ 269 nm ($\epsilon$ 9,400) and 276 nm ($\epsilon$ 8,600) $\nu_{max}$ (CHBr$_3$) 3350 (NH), 1780 (β-lactam), 1710 (CO$_2$R), 1680 and 1505 (CONH), and 1445 (P-C(aryl)) cm$^{-1}$, $\tau$ (CDCl$_3$) 4,39 (C$_{(7)}$-H,$dd$,J 4.5 and 9 Hz), 5.19 (C$_{(6)}$-H, $d$, J 4.5 Hz) 4.75 and 4.85 (CH$_2$-P, four major signals of two AB-q J$_{P-H}$ 16 Hz), 6.05 and 6.68 (C$_{(2)}$ — CH$_2$ two $dd$, J$_{H-H}$ 18 Hz, J$_{P-H}$ 3–4 Hz). [Found: C, 59.3; H, 4.5; I, 13.4; N, 2.6; P, 3.4; S, 7.3. C$_{45}$H$_{38}$IN$_2$O$_4$PS$_2$ (892.8) requires C, 60.5; H, 4.3; I, 14.2; N, 3.1; P, 3.5; S, 7.2%].

EXAMPLE 2

[4-Diphenylmethoxycarbonyl-7β-(2-thienylacetamido) ceph-3-em-3-ylmethyl]-triphenylphosphonium bromide A solution of diphenylmethyl 3-bromomethyl-7β-(2-thienylacetamido)ceph-3-em- 4-carboxylate (300mg.), Rf 0.6 in benzene (5 ml.) was treated with triphenylphosphine (140 mg.) and the total warmed to 50° for 10 minutes. After the mixture had stood at room temperature for a further hour it was diluted with ether and the precipitated solid was collected by filtration. This material was washed thoroughly with ethyl acetate and ether, and on drying in vacuo gave the phosphonium bromide (250 mg.) Rf 0.0 m.p. 135° – 140° C (decomp.) $[\alpha]_D + 12°$ (tetrahydrofuran), $\nu_{max}$ (CHBr$_3$) 3410 (NH), 1784 (β-lactam), 1710 (CO$_2$R), 1680 and 1515 (CONH) and 1442 (P-C aryl.) cm.$^{-1}$ $\tau$ (CDCl$_3$) 4.38 (C$_{(7)}$-H, $dd$, J 4.5 and 9 Hz), 5.19 (C$_{(6)}$-H, $d$, J 4.5 Hz), 4.62 and 4.8 (CH$_2$ - P, two $d$, J$_{P-H}$ 16 Hz), 6.02 and 6.6 (C$_{(2)}$ — CH$_2$, two $dd$, J$_{H-H}$ 18 Hz and J$_{P-H}$ 3–4 Hz).

EXAMPLE 3

[4-Diphenylmethoxycarbonyl-7β-(2-thienylacetamido) ceph-3-em-3-ylmethyl]-triphenylphosphonium chloride Triphenylphosphine (123 mg. 0.5 m mole.) and diphenylmethyl 3-chloromethyl-7β-(2-thienylacetamido) ceph-3-em-4-carboxylate (266 mg., 0.5 m mole) were melted together for 1 hour under nitrogen at 114°–130°. The black-red product with triturated with tetrahydrofuran to give a brown solid (A) (150 mg.), m.p. 103°–120° (a 1% solution in tetrahydrofuran containing about 20% dimethylsulphoxide was too opaque for polarimetry), $\lambda\lambda_{max}$ 268 nm ($\epsilon$ 10,600), 275 nm ($\epsilon$ 9,700), $\nu_{max}$ (CHBr$_3$) 1770, 1707, 1675, 1510, 1430, 1250, and 742 cm$^{-1}$; n.m.r. (CDCl$_3$ and $d_6$ - DMSO at 60 MHz) gave evidence only for aromatic protons and the thienylacetamido-methylene group. A comparison with the physical constants for the analogous phosphonium iodide suggests that this product (A) contained the title compound.

EXAMPLE 4

[4-Diphenylmethoxycarbonyl-7β-(2-thienylacetamido)ceph-3-em-3-ylmethyl]tri-n-butyl-phosphonium iodide A solution of diphenylmethyl 3-iodomethyl-7β-(2-thienylacetamido)ceph-3-em-4-carboxylate (4.9 g.) in ethyl acetate (90 ml.) was stirred in the dark at room temperature and treated, over 15 minutes, with a solution of tri-n-butylphosphine (3.1 g., ca. 2 equivs.) in ethyl acetate (50 ml.). The solution was stirred for a further 45 minutes and precipitated into petroleum-ether to give the phosphonium iodide (3.448 g.), m.p. 120°–125° (decomp), $[\alpha]_D$ - 43°(N,N-dimethylformamide), R$_F$ 0.0, inflexion (EtOH) at 259 nm. ($\epsilon$7,100), $\nu_{max}$. (CHBr$_3$) 3410 (-NH), 1786 (β-lactam), 1708 (ester), and 1686 and 1510 cm. $^{-1}$ (—$\tau$ (CDCl$_3$) 4.22 (C$_{(7)}$-H, $dd$, J 5 and 9 Hz.), 4.87 (C$_{(6)}$-H $d$, J 5 Hz), 5.80 and 6.11 (C$_{(2)}$-CH$_2$, two $dd$, J$_{H-H}$ 18 Hz., J$_{P-H}$ 3–4 Hz). [Found: C, 55.3; H, 6.0; I, 15.7; N, 3.1; P, 3.7 C$_{39}$H$_{50}$IN$_2$O$_4$PS$_2$ (832.8) requires C, 56.2; H, 6.1; I, 15.1; N, 3.4; P, 3.7%].

EXAMPLE 5

[4-Diphenylmethoxycarbonyl-7β-(2-thienylacetamido)ceph-3-em-3-ylmethyl] triphenylphosphonium bromide, 1β-oxide A solution of diphenylmethyl 3-bromomethyl-7β-(2-thienylacetamido)ceph-3-em-4-carboxylate 1β-oxide (599 mg., 1 mmole) in methylene chloride (25 ml.) was stirred at room temperature and treated, over 15 minutes, with a solution of triphenylphosphine (787 mg., ca. 3 equivs.) in methylene chloride (5 ml.). The solution was stirred for a further 60 minutes at room temperature, the solvent removed by rotary evaporation, and the residual foam triturated with ethyl acetate to give white crystals of the title compound (752 mg., 87%), R$_F$ 0.0 m.p. 133° (decomp), $[\alpha]_D$ - 16° (N,N-dimethylformamide) $\nu_{max}$ (CHBr$_3$) 3390 (-NH), 1798 (β-lactam), 1710 (—CO$_2$R), 1690 and 1510 (—CONH—) 1440 (P-C (aryl)) and 1030 cm.$^{-1}$ (S → O), $\lambda_{max}$ 271 nm. ($\epsilon$ 8,300) and 278 nm. ($\epsilon$ 9,700), $\tau$(CDCl$_3$) 3.96 (C$_{(7)}$-H, $dd$, J 5 and 10 Hz), 4.40 and 4.56 (CH$_2$-P, two $d$, J$_{P-H}$ 14 Hz), 4.88 and 6.56 (C$_{(2)}$-CH$_2$, two $dd$ J$_{H-H}$ 19 Hz., J$_{P-H}$ 3 Hz.), 5.05 (C$_{(6)}$-H, $d$ J 5 Hz.) [Found: C, 61.0; H, 4.4; Br, 8.8; N, 2.8; P, 3.8. C$_{45}$H$_{38}$BrN$_2$O$_5$PS$_2$ (861.8) requires C, 62.8; H, 4.45; Br, 9.3; N, 3.25; P, 3.6%].

EXAMPLE 6

[4-Diphenylmethoxycarbonyl-7β-(2-thienylacetamido)ceph-2-em-3-ylmethyl] triphenylphosphonium chloride A solution of diphenylmethyl 3-chloromethyl-7β-(2-thienylacetamido)ceph-2-em-4-carboxylate (2.3 g.) in ethyl acetate (20 ml.) was treated with triphenylphosphine (2.3 g., ca. 2 equivs.) and the mixture refluxed for 5 hours. The solution was cooled and the insoluble product isolated by filtration. This material was precipitated from acetone (containing some chloroform) solution by petroleum-ether to give the phosphonium salt (500 mg.) as an amorphous solid $[\alpha]_D$ + 68.5°(CHCl$_3$), $\lambda_{max.}$ (CHCl$_3$) 269.5 and 276.5 nm. ($\epsilon$ 8,880 and 7,620), $\nu_{max.}$ (CHBr$_3$) 3440 (NH), 1780 ($\beta$-lactam), 1680 and 1510 (—CONH—), and 1445 (P-C aryl) cm,$^{-1}$, $\tau$(CDCl$_3$) 3.61 (C$_{(2)}$-H), 4.4 (C$_{(7)}$-H, dd, J 4.5 and 9 Hz), 4.75 (C$_{(6)}$-H, not well resolved), 5.04 and 5.18 (CH$_2$-P, part of two AB-q, J$_{P-H}$ 13 Hz.).

EXAMPLE 7

Diethyl[4-diphenylmethoxycarbonyl-7$\beta$-(2-thienylacetamido) ceph-3-em-3-ylmethyl]phosphonate A solution of diphenylmethyl 3-iodomethyl-7$\beta$-(2-thienylacetamido)ceph-3-em-4-carboxylate (315 mg.) in ethyl acetate (4 ml.) was treated with triethylphosphite (0.3 ml.) and the mixture refluxed for 1½ hours. Dilution of the solution with petroleum ether (40°–60° C fraction) gave the phosphonate (270 mg.) as an amorphous solid, $[\alpha]_D$ + 2.5° (CHCl$_3$), inflexions at 234 and 264 nm. ($\epsilon$ 13,960 and 6,850) $\nu_{max.}$ (CHBr$_3$) 1775 ($\beta$-lactam), 1718 (CO$_2$R), 1675 and 1508 (CONH) cm$^{-1}$, $\tau$ (CDCl$_3$) 4.25 (C$_{(7)}$-H, dd,J 4.5 and 9 Hz.), 5.05 (C$_{(6)}$-H, d,J 4.5 Hz), 6.07 and 8.82 (P—O—C$_2$H$_5$, qu and t, J$_{H-H}$ = J$_{P-H}$ 7.5 Hz.), 6.50 (C$_{(2)}$-CH$_2$), and 6.55 and 6.94 (-CH$_2$-P$^0$-, two quartets, J$_{H-H}$ 13 Hz., J$_{P-H}$ 24 Hz.).

EXAMPLE 8

[4-Diphenylmethoxycarbonyl-7$\beta$-(2-thienylacetamido)ceph-3-em-3-ylmethyl] tri-n-butylphosphonium bromide A solution of diphenylmethyl 3-bromomethyl-7$\beta$-(2-thienylacetamido)ceph-3-em-4-carboxylate (583 mg.) in ethyl acetate (5 ml.) was treated with a solution of tri-n-butylphosphine (0.3 ml., ca. 2 equivalents) in ethyl acetate (2 ml.). After 10 minutes at room temperature the mixture was diluted with petroleum ether to give the phosphonium salt (690 mg.) as an amorphous solid, m.p. 65° – 70° $[\alpha]_D{}^{23}$ – 35° (c 1.0 CHCl$_3$), inflexion at 237 nm. ($\epsilon$ 12,460) and 258 nm. ($\epsilon$ 6,550), $\nu_{max}$ 1770 ($\beta$-lactam), 1702 (CO$_2$R), 1670 and 1530 (CONH) and 693 (phenyl) cm.$^{-1}$; $\tau$ (CDCl$_3$) 4.22 (C$_{(7)}$-H dd, J 4.5, 9 Hz.), 4.93 (C$_{(6)}$-H, d, J 4.5 Hz.), 5.5 to 6.1 (C$_{(2)}$-CH$_2$ and =C-CH$_2$P$^+$, unresolved m), 7.62 (P$^+$CH$_2$CH$_2$CH$_2$CH$_3$, m), 8.55 (P$^+$CH$_2$CH$_2$CH$_2$CH$_3$, m) and 9.1 (P$^+$CH$_2$CH$_2$CH$_2$CH$_3$, d, J 6 Hz.).

Treatment of this material in ethanol solution with ethoxycarbonylmethylenetriphenylphosphorane (pKa 8.95) gave no chromophore at 388 nm corresponding to the phosphorane derived from the title compound. However, treatment with carbamoylmethylenetriphenylphosphorane (pKa 11) gave the chromophore at 388 nm, corresponding to the phosphorane (pKa values in 80%-aqueous ethanol determined by S. Fliszar, R. F. Hudson and G. Salvadori, Helv.Chim.Acta., 1963 46,1580).

EXAMPLE 9

[7$\beta$-Formamido-4-(2,2,2-trichloroethoxycarbonyl)-ceph-3-em-3-ylmethyl]triphenylphosphonium bromide 1$\beta$-oxide A solution of 2,2,2-trichloroethyl 3-bromomethyl-7$\beta$-formamidoceph-3-em-4-carboxylate 1$\beta$-oxide [334 mg. prepared as described in Preparation A 3(a) and (b)(i) and Example B3(i) of copending Application No. (Ceph 118/131/132/143)] in tetrahydrofuran (6 ml.) was treated with a solution of triphenylphosphine (390 mg. ca. 2 equivalents) in tetrahydrofuran (3 ml.). After 30 minutes at room temperature the solvent was removed in vacuo. The residue was washed thoroughly with ether (to remove triphenylphosphine) to give the phosphonium bromide (514 mg.) as an amorphous solid, m.p. 159°–161° (decomp.), $[\alpha]_D$ + 11.30° (CHCl$_3$), $\lambda_{max}$ (CHCl$_3$) 270 nm. ($\epsilon$ 9,780), 277 nm. ($\epsilon$ 10,370) and 290 nm. ($\epsilon$ 8,530), $\nu_{max}$ (CHBr$_3$) 3360 (NH), 1790 ($\beta$-lactam), 1720 (CO$_2$R), 2730, 1680, and 1500 (HCONH), 1435 (P-aryl) and 1020cm$^{-1}$ (SO),$\tau$(DMSO-d$_6$) 1.5 (NH, d, J 9 Hz.), 1.82 (HCONH), 4.02 (C-7 H, dd, J 4.5 and 9 Hz.), 4.69 (C-6 H, d, J 4.5 Hz.), 4.79 (CH$_2$-P, two broad s, J$_{P-H}$ 17 Hz.), 5.19 and 5.44 (CH$_2$CCl$_3$, AB-q,J 12 Hz) and 6.04 (C-2 CH$_2$ broad [degenerate AB-q]).

EXAMPLE 10

(4-t-Butoxycarbonyl-7$\beta$-formamidoceph-3-em-3-ylmethyl)triphenylphosphonium bromide 1$\beta$-oxide A solution of t-butyl 3-bromomethyl-7$\beta$-formamidoceph-3-em-4-carboxylate 1$\beta$-oxide [786 mg. prepared as described in Preparation A4(a), (b)(i) and (c) and Example B4(i) of copending Application No. (ceph 118/131/132/143)] in tetrahydrofuran (10 ml.) was treated with a solution of triphenylphosphine (1.05 g., ca 2 equivalents) in tetrahydrofuran (5 ml.). After 1 hour at room temperature the precipitated solid was collected by filtration and washed with ether to give the phosphonium bromide (800 mg.) as an amorphous solid, m.p. 169°–171° (decomp.), $[\alpha]_D$ + 18.1° (CHCl$_3$), $\lambda_{max.}$ (CHCl$_3$) 270 nm. ($\epsilon$ 10,100) and 277 nm. ($\epsilon$ 10,540) and inflexion at 290 nm. ($\epsilon$ 8,850), $\nu_{max}$ (CHBr$_3$) 3360 (NH), 1790 ($\beta$-lactam), 1700 (CO$_2$R), 2740, 1698, and 1502 (HCONH), 1440 (P-aryl) and 1029 cm.$^{-1}$ (SO), $\tau$ (DMSO-d$_6$) 1.54 (NH, d, J 9 Hz.), 1.8 (HCONH), 4.03 (C$_{(7)}$-H, dd,J 4.5,9 Hz.), 4.70 (C$_{(6)}$-H, d J 4.5 Hz.), 4.72 and 4.88 (CH$_2$-P, centres of two AB-q, J$_{H-H}$ ca. 15 Hz.), 6.15 (C$_{(2)}$-CH$_2$, broad s), and 8.71 (t-butyl).

EXAMPLE 11

[7$\beta$-Phenylacetamido-4-(2,2,2-trichloroethoxycarbonyl)-ceph-3-em-3-ylmethyl]-triphenylphosphonium bromide 1$\beta$-oxide A solution of triphenylphosphine (52 mg., 2 equiv.) in methylene chloride (0.5 ml.) was added to a solution of 2,2,2-trichloroethyl 3-bromomethyl-7$\beta$-phenylacetamidoceph-3-em-4-carboxylate 1$\beta$-oxide [56 mg., 0.1 mmole prepared as described in Preparation A2(i) and Example B2(i) of copending Application No. (ceph 118/131/132/143)], in methylene chloride (0.5 ml.). After 30 minutes had elapsed, TLC (methylene chloride - acetone; 4:1) showed that no starting bromoester remained and that a new product, R$_F$ 0.0, had resulted. The solvent was evaporated and the residual foam was triturated with ethyl acetate to give the title phosphonium salt, m.p. 150°–154° (dec.), $\lambda_{max.}$ 268 nm (E$_{1cm.}{}^{1\%}$ 101) and 275 (E$_{1cm.}{}^{1\%}$ 101) $\nu_{max.}$ (CHBr$_3$) 3400 (NH), 1803 (azetidin-2-one), 1732 (CO$_2$R), 1692 and 1510 (CONH) and 1034 cm.$^{-1}$ (SO).

EXAMPLE 12

[4-t-Butoxycarbonyl-7β-phenoxyacetamidoceph-3-em-3-ylmethyl]-triphenylphosphonium Bromide A solution of triphenylphosphine (1.95 g, 2 equiv.) in ethyl acetate (6 ml) was added to a solution of t-butyl 3-bromomethyl-7β-phenoxyacetamidoceph-3-em-4-carboxylate (1.80 g, 3.72 mmole) in ethyl acetate (4 ml.). The mixture was stirred for 1 hour, and the precipitated solid was filtered off, washed with ether and dried to give the title phosphonium salt (2.42 g, 87.5%), m.p. 144° to 146°, $[\alpha]_D^{22}$ +31° (C 0.95; Me$_2$SO), $\lambda_{max.}$ (EtOH) 268 nm ($\epsilon$ 11,300) and 275 nm ($\epsilon$ 10,400), $\nu_{max.}$ (Nujol) 3400 (NH), 1778 (azetidin-2-one), 1692 and 1520 (CONH), 1690 (CO$_2$R) and 1430 cm$^{-1}$ (P$^+$-C$_6$H$_5$), $\tau$ (Me$_2$SO-d$_6$) 0.89 (1H,$d$, $j$ 8 Hz; NH), 2.66 and 2.99 (2H and 3H, 2 m; C$_6$H$_5$O), 4.29 (1H, centres of two AB-quartets, J$_{H-H}$ 15 Hz, J$_{P-H}$ 16 Hz; C$_3$-CH$_2$P$^+$), 5.33 (2H, $s$; C$_6$H$_5$OCH$_2$), 8.76 (9H, $s$; CO$_2$C(CH$_3$)$_3$).

EXAMPLE 13

[4-t-Butoxycarbonyl-7β-phenoxyacetamidoceph-3-em-3-ylmethyl]-triphenylphosphonium Bromide, 1β-oxide A solution of t-butyl 3-bromomethyl-7β-phenoxyacetamidoceph-3-em-4-carboxylate, 1β-oxide (500 mg, 1 mmole) and triphenylphosphine (525 mg, 2 equiv.) in a mixture of methylene chloride (4 ml) and tetrahydrofuran (3 ml) was stirred at ca. 25° for 1 hour. The precipitated solid was filtered off, washed with ether and dried to give the title phosphonium salt, 1β-oxide (631 mg, 83%), m.p. 192°, $[\alpha]_D^{24.5}$ + 9.7° (C 1.03; Me$_2$SO), $\lambda_{max.}$ (EtOH) 269.5 nm ($\epsilon$ 10,100) and 276 nm ($\epsilon$ 10,800), $\nu_{max.}$ (CHBr$_3$) 3375 (NH), 1794 (azetidin-2-one), 1702 (CO$_2$R), 1690 and 1518 (CONH), 1440 (P$^+$-C$_6$H$_5$) and 1030 cm$^{-1}$ (S → O), $\tau$ (Me$_2$SO-d$_6$) 1.81 (1H, $d$, J 9.5 Hz; NH), 2.66 and 2.99 (2H and 3H, 2m; C$_6$H$_5$O), 3.97 (1H,$dd$, J 9.5 and 5 Hz; C$_7$-H), 4.75 and 4.91 (2H, centres of 2 AB-quartets, J$_{H-H}$ 15 Hz, J$_{P-H}$ ca15 Hz; C$_3$-CH$_2$P), 4.75 (1H,$d$, J 5Hz; C$_6$-H), 6.16 (2H, broad $s$; C$_2$-H$_2$), 8.76 (9H, $s$; CO$_2$C(CH$_3$)$_3$) (Found: C, 59.6; H, 5.1; Br, 11.7; N, 3.2. C$_{38}$H$_{38}$BrN$_2$O$_6$PS (761.7) requires C, 59.9; H, 5.0; Br, 10.5; N, 3.7%).

EXAMPLE 14 a. 2,2,2-Trichloroethyl 3-Bromomethyl-7β-phenylacetamidoceph-3-em-4-carboxylate

A solution of 2,2,2-trichlorethyl 3-bromomethyl-7β-phenylacetamidoceph-3-em-4-carboxylate, 1β-oxide (560 mg, 1 mmole) in dry methylene chloride (25 ml) was cooled to below −20° and a solution of phosphorus tribromide (0.14 ml, 1.5 equiv.) in methylene chloride (ca. 1.3 ml) was added over a period of 15 minutes. The mixture was kept at −20° for a further 15 minutes, and then washed with 4%-sodium hydrogen carbonate solution and water (2 × 10 ml. of each), dried (MgSO$_4$), and evaporated to give the title ester as a pale-yellow foam (419 mg, 77%), $[\alpha]_D$ − 33.6° (C 1.06; CHCl$_3$), $\lambda_{max.}$ (EtOH) 278 nm ($\epsilon$ 7,850), $\nu_{max.}$ (CHBr$_3$) 3430 (NH), 1790 (azetidin-2-one), 1740 (CO$_2$R) and 1682 and 1508 cm$^{-1}$ (CONH), $\tau$ (CDCl$_3$) 2.69 (5H, $s$; C$_6$H$_5$), 3.60 (1H,$d$, J 10 Hz; NH), 4.16 (1H,$dd$, J 10 and 5 Hz; C$_7$-H), 4.98 and 5.22 (2H, AB-q, J 12 Hz; CH$_2$CCl$_3$), 5.00 (1 H,$d$, J 5 Hz; C$_6$-H), 5.60 (2H, $s$, C$_3$-CH$_2$Br), 6.23 and 6.60 (2H, AB-q, J 18 Hz; C$_2$-H$_2$), 6.38 (2H, $s$; C$_6$H$_5$CH$_2$).

b. [7β-Phenylacetamido-4-(2,2,2-trichloroethoxycarbonyl)ceph-3-em-3-ylmethyl]-triphenylphosphonium Bromide A solution of triphenylphosphine (4.98 g, 2 equiv.) in ethyl acetate (30 ml) was added over a period of 15 minutes to a stirred solution of 2,2,2-trichloroethyl 3-bromomethyl-7β-phenylacetamidoceph-3-em-4-carboxylate (5.2 g, ca. 9.5 mmole) in ethyl acetate. The mixture was stirred in the absence of light for 2 hours when the precipitated solid was filtered off, washed with ethyl acetate and dried to give the title phosphonium salt (6.17 g, 81%), $\lambda_{max.}$ (EtOH) 268.5 nm ($\epsilon$ 10,450) and 275.5 nm ($\epsilon$ 10,050), $\nu_{max.}$ (CHBr$_3$) 3412 (NH), 1784 (azetidin-2-one), 1722 (CO$_2$R), 1678 and 1498 (CONH) and 1440 cm$^{-1}$ (P-$^+$C$_6$H$_5$).

EXAMPLE 15 a. t-Butyl 3-Bromomethyl-7β-formamidoceph-3-em-4-carboxylate

A solution of t-butyl 3-bromomethyl-7β-formamidoceph-3-em-4-carboxylate, 1β-oxide (3.95 g, 10 mmole) in dry methylene chloride (85 ml) was cooled to −20° and a solution of phosphorus tribromide (1.43 ml, 15 mmole) in dry methylene chloride (9 ml) was added. The mixture was kept at −20° for 17 minutes, when 5% sodium hydrogen carbonate solution was added until the mixture was alkaline. The organic layer was washed with water, dried (MgSO$_4$), and evaporated to give the title ester as a cream foam (3.45 g, 91%), $[\alpha]_D^{22}$ + 19.3° (C 0.91; CHCl$_3$), $\lambda_{max.}$ (EtOH) 270.5 nm ($\epsilon$ 5,300), $\nu_{max.}$ (CHBr$_3$) 3420 (NH), 1790 (azetidin-2-one), 1720 (CO$_2$R) and 1700 and 1505 cm$^{-1}$ (CONH), $\tau$ (CDCl$_3$) 1.76 (1H, $s$; CHO), 3.25 (1H,$d$,J 9 Hz; NH), 4.15 (1H,$dd$,J 9 and 5 Hz; C$_7$-H), 5.02 (1H,$d$, J 5 Hz; C$_6$-H), 5.61 (2H, $s$; C$_3$-CH$_2$Br), 6.30 and 6.54 (2H, AB-q, J 18 Hz; C$_2$-H$_2$), 8.44 (9H,s; CO$_2$C(CH$_3$)$_3$).

b. [4-t-Butoxycarbonyl-7β-formamidoceph-3-em-3-ylmethyl]-triphenylphosphonium Bromide i. A solution of t-butyl 3-bromomethyl-7β-formamidoceph-3-em-4-carboxylate (340 mg, 0.9 mmole) in ethyl acetate (5 ml) was treated with a solution of triphenylphosphine (520 mg. 2 mmole) in ethyl acetate (5 ml). The mixture was warmed to 50° for a few minutes and then stored at 23° for 1½ hours. The precipitated solid was filtered off, washed with ether, and dried to give the title phosphonium salt (270 mg, 47%), $\lambda_{max.}$ (EtOH) 269 nm ($\epsilon$ 9,350) and 275.5. nm ($\epsilon$ 9,200), $\nu_{max.}$ (CHBr$_3$) 3430 (NH), 1790 (azetidin-2-one), 1706 (CO$_2$R), 1700 and 1510 (CONH) and 1445 cm$^{-1}$ (P$^+$-C$_6$H$_5$), $\tau$ (Me$_2$SO-d$_6$) 0.85 (1H,$d$, J 8.5 Hz; NH), 1.84 (1H, $s$; CHO), 4.27 (1H, $dd$, J 8.5 and 5 Hz; C$_7$-H), 4.68 (1H, $d$, J 5Hz; C$_6$-H), 4.79 and 4.95 (2H, centres of two AB-quartets, J$_{H-H}$ 14 Hz, J$_{P-H}$ 16 Hz; C$_3$-CH$_2$P$^+$), 8.77 (9H, $s$; CO$_2$C(CH$_3$)$_3$).

ii. A solution of [4-t-butoxycarbonyl-7β-formamidoceph-3-em-3-ylmethyl]-triphenylphosphonium bromide 1β-oxide (327.5 mg. 0.5 mmole) in dry methylene chloride (3 ml) was cooled to −20° and treated with a 10%-solution of phosphorus tribromide in dry methylene chloride (0.71 ml, 1.5 equiv.). The mixture was kept at −20° for 20 minutes, when gradual addition of light petroleum (b.p. 40° to 60°) precipitated an oil which solidified on trituration. The solid was filtered off, washed with light petroleum and dried to give the title phosphonium salt (317 mg, 99%). The p.m.r. spectrum ($Me_2SO-d_6$) of the product was not as well resolved as that obtained in (i) above, but supported the assigned structure.

EXAMPLE 16 a. 2,2,2-Trichloroethyl 3-Bromomethyl-7β-formamidoceph-3-em-4-carboxylate

A stirred solution of 2,2,2-trichloroethyl 3-bromomethyl-7β-formamidoceph-3-em-4-carboxylate, 1β-oxide (5.77 g, 12.3 mmole) in a mixture of dry methylene chloride (400 ml) and dry tetrahydrofuran (50 ml) was cooled to −20° and treated with a solution of phosphorus tribromide (1.77 ml, 1.5 equiv.) in dry methylene chloride (9 ml.). The reaction mixture was stirred at −20° for 35 minutes when an excess of saturated aqueous sodium hydrogen carbonate solution was added. The organic phase was washed with water, dried ($MgSO_4$), and evaporated to give the title ester as a cream foam (5.87 g, 100%), $[\alpha]_D$ - 23.3° (C 1.10; tetrahydrofuran), $\lambda_{max.}$ (EtOH) 277.5 nm ($\epsilon$ 6,800), $\nu_{max.}$ ($CHBr_3$) 3450 (NH), 1790 (azetidin-2-one), 1740 ($CO_2R$) and 1700 and 1503 $cm^{-1}$ (CONH), $\tau$ ($CDCl_3$) 0.03 (1H,$d$, J 8 Hz; N$\underline{H}$), 1.87 (1H,$s$; C$\underline{H}$O), 4.16 (1H,$dd$,J 8 and 5 Hz; $C_7$-$\underline{H}$), 4.75 (1H,$d$, J 5 Hz; $C_6$-$\underline{H}$), 4.80 and 5.00 (2H, AB-q, J 13 Hz; $C\underline{H}_2CCl_3$), 5.47 (2H, centre of an AB-q; $C_3$-$C\underline{H}_2Br$), 6.14 and 6.39 (2H,AB-q, J 17 Hz; $C_2$-$\underline{H}_2$).

b. [7β-Formamido-4-(2,2,2-trichloroethoxycarbonyl)-ceph-3-em-3-ylmethyl]-triphenylphosphonium Bromide A solution of triphenylphosphine (1.06 g, 2 equiv.) in ethyl acetate (5 ml) was added to a stirred solution of 2,2,2-trichloroethyl 3-bromomethyl-7β-formamidoceph-3-em-4-carboxylate (0.91 g, 2 mmole) in ethyl acetate (5 ml). The mixture was stirred at ca. 20° for 45 minutes and then warmed to 45° for 10 minutes. The precipitated solid was filtered off, washed with ethyl acetate and ether, and dried to give the title phosphonium salt (1.06 g, 74%), m.p. 151° to 153° (dec.), $[\alpha]_D$ + 92° (C 1.0; $CHCl_3$), $\lambda_{max.}$ (EtOH) 268.5 nm ($\epsilon$ 9,000) and 275 nm ($\epsilon$ 9,000), $\nu_{max.}$ ($CHBr_3$) 3430 (NH), 1795 (azetidin-2-one), 1730 ($CO_2R$), 1700 (CONH) and 1445 $cm^{-1}$ ($P^+$-$C_6H_5$), 0.91 (1H,$d$, J 9 Hz; N$\underline{H}$), 4.25 (1H,$dd$, J 9 and 5 Hz; $C_7$-$\underline{H}$), 4.67 (1H,$d$, J 5 Hz; $C_6$-$\underline{H}$), 4.77 and 4.93 (2H, centres of two collapsed AB-quartets, $J_{P-H}$ 16 Hz; $C_3$-$C\underline{H}_2P^+$, 5.25 and 5.45 (2l H, AB-q, J 12 Hz; $C\underline{H}_2CCl_3$) (Found: C, 46.9; H, 3.7; N, 3.7; P, 3.7; S, 3.9%; total halogen content, 3.9 equiv./mole compound. $C_{29}H_{25}BrCl_3N_2O_4PS$ (714.9) requires C, 48.7; H, 3.5; N, 3.9; P, 4.3; S, 4.5%; total halogen content 4 equiv./mole compound).

EXAMPLE 17 a. 2,2,2-Trichloroethyl 3-Bromomethyl-7β-phenoxyacetamidoceph-3-em-4-carboxylate.

A stirred solution of 2,2,2-trichloroethyl 3-bromomethyl-7β-phenoxyacetamidoceph-3-em-4-carboxylate 1β-oxide (5.73 g, 9.96 mmole) in dry methylene chloride (100 ml) was cooled to −50° and treated with phosphorus tribromide (1.42 ml, 1.48 equiv.) The reaction mixture was kept at −50° for 1 hour and then allowed to warm to 0° over a period of 30 minutes. An excess of 3%-sodium hydrogen carbonate solution was added, the mixture was stirred for 5 minutes, and the organic phase was washed with water (50 ml), dried ($MgSO_4$) and evaporated to a foam (6.3 g). Chromatography on Kieselgel G (Merck; 200 g) with 25%-ethylacetate in benzene as eluant gave the title ester as a pale-yellow foam (2.77 g, 50%), $[\alpha]_D^{24}$ - 2.7° (C 1.03; $Me_2SO$), $\lambda_{max}$ (EtOH) 269 nm ($\epsilon$ 8,700) and 275.5 nm ($\epsilon$ 9,050), $\nu_{max}$ ($CHBr_3$), 3410 (NH), 1780 (azetidin-2-one), 1742 ($CO_2R$) and 1690 and 1512 $cm^{-1}$ (CONH), $\tau$ ($Me_2SO-d_6$) 0.84 (1H,$d$, J 8 Hz; N$\underline{H}$), 2.72 and 3.04 (2H and 3H, 2 m; $C_6H_5O$), 4.21 (1H,$dd$, J 8 and 5 Hz; $C_7$-$\underline{H}$), 4.74 (1H,$d$, J 5 Hz; $C_6$-$\underline{H}$), 4.79 and 5.00 (2H, AB-q, J 12 Hz; $C\underline{H}_2CCl_3$), 5.39 (2H, $s$; $C_6H_5OC\underline{H}_2$), 5.41 and 5.56 (2H, AB-q, J 11 Hz; $C_3$-$C\underline{H}_2Br$), 6.15 and 6.39 (2H, AB-q, J 18 Hz; $C_2$-$\underline{H}_2$).

b. [7β-Phenoxyacetamido-4-(2,2,2-trichloroethoxycarbonyl)ceph-3-em-3-ylmethyl]-triphenylphosphonium Bromide A solution of 2,2,2-trichloroethyl 3-bromomethyl-7β-phenoxyacetamidoceph-3-em-4-carboxylate (ca. 7 mmole) in ethyl acetate (25 ml) was stirred at 25° in the absence of light while a solution of triphenylphosphine (3.67g, 2 equiv.) in ethyl acetate (40 ml) was added over 10 minutes. The reaction mixture was stirred at 25° for 3½ hours and the precipitated solid was filtered off washed with ethyl acetate and dried, (5.62 g), and redissolved in chloroform (40 ml). The filtered solution was diluted with a mixture of ether (20 ml) and light petroleum (b.p. 40° to 60°; 10 ml) and stirred for 30 minutes, and the precipitated solid was filtered off and dried to give the title phosphonium salt (5.47 g, 95%), m.p. 125 to 135°, $[\alpha]_D^{23}$+4.4° (C 1.06; ($Me_2SO$), $\lambda_{max.}$ (EtOH) 268 nm ($\epsilon$ 9,250) and 275 nm ($\epsilon$ 8,850), $\nu_{max.}$ ($CHBr_3$) 3430 (NH), 1794 (azetidin-2-one), 1730 ($CO_2R$), 1693 and 1520 (CONH) and 1442 $cm^{-1}$ ($P^+$-$C_6H_5$).

EXAMPLE 18 a. Diphenylmethyl 3-Bromomethyl-7β-phenoxyacetamidoceph-3-em-4-carboxylate, 1β-Oxide Peracetic acid (37.6%; 2.4 ml. 11.63 mmole) was added over a period of 20 minutes to a stirred solution of diphenyl methyl 3-methyl-7β-phenoxyacetamidoceph-3-em-4-carboxylate (6.0 g, 11.65 mmole) in 1,2-dichloroethane (200 ml.). The mixture was stirred for a further 30 minutes, washed with water and 3%-sodium hydrogen carbonate solution (50 ml of each) dried, and concentrated to ca. 100 ml. The solution was made up to 300 ml with 1,2-dichloroethane and part (250 ml) was stirred and cooled to −9°, and 1,3-dibromo-5,5-dimethylhydantoin (2.08 g, 7.28 mmole) was added. The stirred, cooled mixture was irradiated with a 125-watt medium-pressure mercury-arc, with a Pyrex-filter, for 1 hour at −9° in an atmosphere of nitrogen. The reaction mixture was filtered and washed with 3%-sodium hydrogen carbonate solution (2 × 100 ml) and water (50 ml.). The aqueous washings were back-washed with 1,2-dichloroethane (50 ml) and the combined organic phases were dried (MgSo$_4$) and concentrated to low volume, whereupon a solid separated. This solid was filtered off, washed with ether, and dried to give the title ester 1β-oxide (2.87 g, 48.5%), m.p. 157° to 160°, $[\alpha]_D^{25}$ −53° (c 0.94, Me$_2$So), $\lambda_{max}$. (EtOH) 268.5 (ε 9,250) and 274.5 nm (ε 9,950), part of which was recrystallised from methanol to give a white solid, m.p. 165° to 167° (dec.), $[\alpha]_D^{25}$−51° (c 0.80; Me$_2$SO), $\lambda_{max}$. (EtOH) 269.5 nm (ε 9,700) and 275.5 nm (ε 10,500), $\nu_{max}$.(CHBr$_3$) 3390 (NH), 1800 (azetidin-2-one), 1725 (CO$_2$R), 1690 and 1515 (CONH), and 1050 cm$^{-1}$ (S → O), τ (Me$_2$SO-d$_6$) 0.81 (1H,d, J 10 Hz; N$\underline{H}$), 2.3 to 2.8 and 2.98 (12H and 4H, 2 m; (C$_6$$\underline{H}_5$)$_2$C$\underline{H}$ and C$_6$$\underline{H}_5$O), 3.84 (1H,dd,J 10 and 5 Hz; C$_7$-$\underline{H}$), 4.91 (1H,d,J 5 Hz; C$_6$-$\underline{H}$), 5.30 (2H,s; C$_6$H$_5$OC$\underline{H}_2$), 5.43 and 5.58 (2H,AB-q, J 10 Hz; C$_3$-C$\underline{H}_2$Br), 5.94 and 6.19 (2H, AB-q, J 19 Hz; C$_2$-$\underline{H}_2$) (Found : C, 56.9, 56.5; H, 4.3, 4.2; Br, 11.85, 12.2; N, 4.1, 4.4; S, 5.3. C$_{29}$H$_{25}$BrN$_2$O$_6$S (609.5) requires C, 57.15; H, 4.1; Br, 13.1; N, 4.6; S, 5.3%).

b. Diphenylmethyl 3-Bromoethyl-7β-phenoxyacetamidoceph-3-em-4-carboxylate

A solution of diphenylmethyl 3-bromomethyl-7β-phenoxyacetamidoceph-3-em-4-carboxylate, 1β-oxide (1.83 g, 3 mmole) in dry methylene chloride (25 ml) was cooled to −25°, and phosphorus tribromide (0.43 ml, 1.5 equiv.) was added over 5 minutes, the temperature of the mixture being kept below −20° during the addition. The reaction mixture was stirred at −20° for 2 hours, diluted with methylene chloride (75 ml), washed with 3%-sodium hydrogen carbonate solution (2 × 50 ml), and water (50 ml), dried, and evaporated to give the title ester as a pale-orange foam (1.515 g, 85%), $\lambda_{max}$. (EtOH) 268.5 nm (ε 6,950), τ (CDCl$_3$) 2.4 to 2.8 and 2.98 (12H and 5H, 2m; (C$_6$$\underline{H}_5$)$_2$C$\underline{H}$, C$_6$$\underline{H}_5$O and N$\underline{H}$), 4.08 (1H, dd, J 9 and 5 Hz; C$_7$-$\underline{H}$), 4.98 (1H, d, j 5 Hz; C$_6$-$\underline{H}$), 5.45 (2H, S; C$_6$H$_5$OC$\underline{H}_2$), 5.71 (2H, s; C$_3$-C$\underline{H}_2$Br), 6.32 and 6.56 (2H, AB-q, J 18 Hz; C$_2$-$\underline{H}_2$).

c. [4-Diphenylmethoxycarbonyl-7β-phenoxyacetamidoceph-3-em-3-ylmethyl]-triphenylphosphonium Bromide A solution of triphenylphosphine (0.99 g, 1.5 equiv.) in ethyl acetate (10 ml) was added to a stirred solution of diphenylmethyl 3-bromomethyl-7β-phenoxyacetamidoceph-3-em-4-carboxylate (ca. 1.49 g, 2.515 mmole) in ethyl acetate (25 ml). The mixture was stirred in the absence of light for 16 hours, and the precipitated solid was filtered off, washed with ethyl acetate and dried to give the title phosphonium salt (1.585 g, 74%), $\lambda_{max}$. (EtOH) 268.5 nm (ε 10,700) and 275.5 nm(ε 9,850), $\nu_{max}$.(CHBr$_3$), 3415 (NH), 1788 (azetidin-2-one), 1710 (CO$_2$R), 1692 and 1620 (CONH) and 1440 cm$^{-1}$ (P$^+$-C$_6$H$_5$).

EXAMPLE 19 a. 7β-Formamido-3-methylceph-3-em-4-carboxylic Acid

7β-Amino-3-methylceph-3-em-4-carboxylic acid (20 g, 93.3 mmole) was added to a mixture of acetic anhydride (30 ml) and formic acid (98 to 100%; 160 ml), previously cooled to 0°. After 30 minutes, when solution had been obtained, the solvents were removed in vacuo and ethyl acetate (200 ml) was added to the residual oil. Some insoluble gelatinous material was removed by filtration and the filtrate was evaporated to give the title acid as a pale yellow foam, $\lambda_{max}$. (pH 6 phosphate) 260.5 nm (E$_{1cm}^{1\%}$ 287).

b. Diphenylmethyl 7β-Formamido-3-methylceph-3-em-4-carboxylate

A solution of diphenyldiazomethane in ether (prepared from benzophenone hydrazone [21 g, 41.8 mmole]) was added to a solution of 7β-formamido-3-methylceph-3-em-4-carboxylic acid (9.7 g, 40.2 mmole) in tetrahydrofuran (150 ml) and the mixture was stirred overnight in the absence of light. The solvents were removed in vacuo and the residual oil was dissolved in methylene chloride (200 ml). The solution was washed with 3%-sodium hydrogen carbonate solution (2 × 100 ml), dried, and evaporated to a yellow oil which was triturated with ethyl acetate-ether to give the title ester as a white crystalline solid (8.15 g, 49.5%), m.p. 136° to 140°, $[\alpha]_D^{23}$ + 38° (c 0.94; Me$_2$SO), $\lambda_{max}$. (EtOH) 258 nm (ε 6,800), $\nu_{max}$. (Nujol) 3330 (NH), 1771 (azetidin-2-one), 1707 (CO$_2$R) and 1655 and 1523 cm$^{-1}$ (CONH), τ (Me$_2$SO-d$_6$) 1.91 (1H, d, J 9.5 Hz; N$\underline{H}$), 1.89 (1H, s; C$\underline{H}$O), 2.4 to 2.8 (10H, m; (C$_6$$\underline{H}_5$)$_2$CH), 3.07 (1H, s; (C$_6$H$_5$)$_2$C$\underline{H}$), 3.19 (1H,dd, J 9.5 and 5 Hz; C$_7$-$\underline{H}$), 4.83 (1H,d, 5 Hz; C$_6$-$\underline{H}$), 6.33 and 6.57 (2H, AB-q, 18 Hz; C$_2$-$\underline{H}_2$), 7.95 (3H, S; C$_3$-C$\underline{H}_2$) (Found: C, 64.55; H, 4.9; N, 6.7; S, 7.7. C$_{22}$H$_{20}$N$_2$O$_4$S (408.5) requires C, 64.7; H, 4.9; N, 6.9; S, 7.85%).

c. Diphenylmethyl 3-Bromomethyl-7β-Formamidoceph-3-em-4-carboxylate 1β-Oxide

A solution of diphenylmethyl 7β-formamido-3-methylceph -3-em-4-carboxylate (6 g, 14.7 mmole) in 1,2-dichloroethane (200 ml) was cooled in an ice-bath and treated with peracetic acid (1 equiv.). The reaction mixture was washed with water (100 ml), 3%-sodium hydrogen carbonate solution (50 ml), dried, and diluted to 400 ml with 1,2-dichloroethane. Part (350 ml) was cooled to 0° and stirred, and a solution of sodium acetate (4.84 g, 59 mmole) in water (25 ml), adjusted to pH 7 by the addition of acetic acid, and 1,3-dibromo-5,5-dimethylhydantoin (2.76 g, 9.65 mmole) were added. The stirred, cooled mixture was irradiated with a 125-watt medium pressure mercury-arc with a Pyrex-filter for 40 minutes at 0 to +3° in an atmosphere of nitrogen. The reaction mixture was washed with 2.5% aqueous sodium metabisulphite solution (200 ml) and water (1 × 150 and 1 × 100 ml). The aqueous washings were backwashed with 1,2-dichloroethane (100 ml) and the combined organic phases were dried (MgSO$_4$) and evaporated. Trituration of the residue with a mixture of ethyl acetate and ether gave the title ester 1β-oxide as a beige solid (3.52 g, 54%), m.p. 155.5° to 157° (dec.), $[\alpha]_D^{23}$ - 18.5° (c 0.96; Me$_2$SO), $\lambda_{max}$. (EtOH) 279.5 nm ($\epsilon$10,100). Part (0.44 g) of the product was crystallised from acetone (25 ml) and ether (10 ml) to give material (0.21 g), m.p. 169.5 to 170° (dec.), $[\alpha]_D^{23}$ - 14.4° (c 0.95; Me₂SO), $\lambda_{max}$. (EtOH) 278.5 nm, $\nu_{max}$. (Nujol) 3280 (NH), 1772 (azetidin-2-one), 1710 (CO₂R), 1664 and 1510 cm⁻¹ (CONH), and 1020 cm⁻¹ (S → O), τ (Me₂SO-d₆) 0.74 (1H,d, J 10 Hz; NH), 0.79 (1H, s; CHO), 2.3 to 2.7 (10 H, m; (C₆H₅)₂CH), 2.98 (1H, s; (C₆H₅)₂ CH), 3.91 (1H,dd, J 10 and 4.5 Hz; C₇-H), 4.91 (1H,d, J 4.5 Hz; C₆-H), 5.35 and 5.58 (2H, AB-q, J 10 Hz; C₃-CH₂Br), 5.95 and 6.20 (2H, AB-q, J 19 Hz; C₂-H₂) (Found: C, 51.4; 50.8; H, 3.95, 3.8; Br, 15.9; N, 5.2, 5.1; S, 6.4. C₂₂H₂₁BrN₂O₅S (503.4) requires C, 52.5; H, 3.8; Br, 15.9; N, 5.6; S, 6.4%).

d. Diphenylmethyl 3-Bromomethyl-7β-formamidoceph-3-em-4-carboxylate

A stirred suspension of diphenylmethyl 3-bromomethyl-7β-formamidoceph-3-em-4-carboxylate, 1β-oxide (2.01 g, 4 mmole) in dry methylene chloride (30 ml) was cooled to −20° and a solution of phosphorus tribromide (0.57 ml, 1.5 equiv.) in dry methylene chloride (10 ml) was added over a period of 10 minutes, the temperature of the mixture being kept at −20°. The mixture was stirred at −20° for 45 minutes, and the organic phase was washed with 4%-sodium hydrogen carbonate solution (2 × 50 ml) and water (50 ml), dried (MgSO₄), and evaporated to give the title ester as a pale orange foam (1.84 g, 94.5%), $\lambda_{max}$. (EtOH) 269 nm ($\epsilon$ 7200), τ (CDCl₃) 1.78 (1H, s; CHO), 2.4 to 2.8 (10H, m; (C₆H₅)₂CH), 3.00 (1H, s; (C₆H₅)₂CH), 3.43 (1H, d, J 9 Hz; NH), 4.10 (1H, dd, J 9 and 5 Hz; C₇-H), 4.99(1H, d, J 5 Hz; C₆-H), 5.70 (2H, s; C₃-CH₂Br), 6.25 and 6.62 (2H, AB-q, J 18 Hz; C₂-H₂).

e. [4-Diphenylmethoxycarbonyl-7β-formamidoceph-3-em-3-ylmethyl]-triphenylphosphonium Bromide A solution of triphenylphosphine (1.47 g, 1.5 equiv.) in ethyl acetate (10 ml) was added to a stirred solution of diphenylmethyl 3-bromomethyl-7β-formamidoceph-3-em-4-carboxylate (1.82 g, 3.725 mmole) in ethyl acetate (50 ml). The mixture was stirred overnight at ca. 20° out of direct light, and the precipitated solid was filtered off, washed with ethyl acetate and dried to give the title phosphonium salt (2.41 g, 86%), $\lambda_{max}$. (EtOH) 268.5 nm ($\epsilon$ 8,700) and 275.5 nm ($\epsilon$8,150), $\nu_{max}$. (CHBr₃) 3440 (NH), (1788 azetidin-2-one), 1710 (CO₂R), 1680 and 1500 (CONH) and 1443 cm⁻¹ (P⁺-C₆H₅), τ (CDCl₃) 1.45 (1H,d, J 9 Hz; NH), 1.73 (1H,s; CHO), 3.57 (1H, s; (C₆H₅)₂CH), 4.32 (1H,dd, J 9 and 5 Hz; C₇-H), 4.62 and 4.78 (2H, centres of 2 AB-quartets, J$_{P-H}$ 16 Hz, J$_{H-H}$ 15 Hz; C₃-CH₂P)⁺, 5.12 (1H, d, J 5 Hz; C₆-H), 6.06 and 6.60 (2H, broadened AB-q, J 18 Hz; C₂-H₂).

EXAMPLE 20 a. Diphenylmethyl 3-(Dimethoxyphosphinylmethyl)-7β(2-thienylacetamido)ceph-3-em-4-carboxylate A solution of diphenylmethyl 3-iodomethyl-7β-(2-thienylacetamido)-ceph-3-em-4-carboxylate (1.26 g.) in ethyl acetate (15 ml.) was treated with trimethylphosphite (1.0 ml.), and the mixture was refluxed for 1.25 hours. The solution was run into petroleum ether (b.p. 40° to 60°) to give the phosphonate (1.2 g., 98%) as an amorphous solid, m.p. ca. 65°, $[\alpha]_D$ - 3.3° (CHCl₃), inflexions at 235 and 260 nm. ($\epsilon$ 13,050 and 7,040), $\lambda_{max}$. (CHBr₃) 3380 (NH), 1780 (β-lactam), 1720 (CO₂R), 1680 and 1510 (CONH), 1250 (P=O), and 1030 cm⁻¹ (P-O-C), τ (DMSO-d₆) 0.86 (NH, d, J 9 Hz.), 4.20 (C₍₇₎-H, dd, J 4.5 and 9 Hz.), 4.81 (C₍₆₎-H, d, J 4.5 Hz.), 6.19 (CH₂CONH) 6.32 and 6.35 (C₍₂₎-CH₂, parts of an AB-q J not measurable), and 6.57 and 6.52 (POCH₃) (Found: C, 56.7; H, 4.9; N, 4.3; P 5.2; S, 10.7. C₂₉H₂₉N₂O₇PS₂ requires C, 56.9; H, 4.8; N, 4.6; P, 5.05; S, 10.5%).

b. 3-(Dimethoxyphosphinylmethyl)-7β-(2-thienyl acetamido) ceph-3-em-4-carboxylic Acid.

A solution of diphenylmethyl 3-(dimethoxyphosphinylmethyl)-7β-(2-thienylacetamido) ceph-3-em-4-carboxylate (750 mg.) in anisole (0.75 ml.) and trifluoroacetic acid (3.0 ml.) was stored at 21° for 5 minutes. The solvents were removed in vacuo and the residue triturated with ether to give the acid (490 mg., 89%) as an amorphous solid, m.p. 150° to 154° (decomp.), $[\alpha]_D$+ 131° (MeOH), $\lambda_{max}$. (0.1M pH6 phosphate buffer) 261.5 nm ($\epsilon$ 8,350), $\nu_{max}$. 3200 (NH), 1780 (β-lactam), 1705 (CO₂H), 1645 (CONH) and 1240 cm.⁻¹ (P=0), τ (DMSO-d₆) 0.95 (NH, d, J 9 Hz.), 2.68 and 3.08 (thienyl), 4.40 (C₍₇₎-H, dd, J 4.5 and 9 Hz.), 4.91(C₍₆₎-H, d, J 4.5 Hz), 6.25 CH₂CONH), 6.32 and 6.40 (POCH₃) and 6.3 to 7.0 (C₍₂₎-CH₂ and CH₂P, complex) (Found: C, 43.9; H, 4.4; N, 6.4; P, 6.55; S, 13.5. C₁₆H₁₉N₂O₇PS₂ requires C, 43.0; H, 4.3; N, 6.3; P, 6.95; S, 14.3%). R$_f$ 0.08 (system C).

EXAMPLE 21 a. t-Butyl 7β-(D-2-t-Butoxycarbonylamino-2-phenylacetamido)-3-chloromethylceph-3-em-4-carboxylate A solution of t-butyl 7β-(D-2-t-butoxycarbonylamino-2-phenylacetamido)-3-hydroxymethyl-ceph-3-cm-4-carboxylate (17.5 g, 0.034 moles) in pure tetrahydrofuran (135 ml.) with pyridine (10.9 ml., 0.135 moles) was added, over a 40 minute period, to a vigorously-stirred solution of thionyl chloride (4.85 ml., 0.068 moles) in pure tetrahydrofuran (100 ml.) at −25°. After a total of 55 minutes stirring the mixture was poured into N-hydrochloric acid containing sodium chloride. The aqueous phase was extracted with ethyl acetate (2 × 300 ml.), and the extracts were combined and washed with water, aqueous sodium bicarbonate solution, and further amounts of water, and then dried, and evaporated in vacuo. A solution of the residue in ethyl acetate was run into petroleum ether (b.p. 40° to 60°) to give the crude chloromethyl derivative (12 g.). Evaporation of the petroleum solution gave a purer sample (2.57 g.). The crude sample was extracted with ether and the ether solution was filtered and run into petroleum ether to give a second purer sample. The purest samples were combined to give the chloromethyl derivative (14.07 g., 77.5%) as an amorphous solid, m.p. 106 to 110° (decomp.), [α] - 24.2° (CHCl₃), $\lambda_{max}$. 265 nm. ($\epsilon$ 6,800), $\nu_{max}$ (CHBr₃) 3410 (NH), 1780 (β-lactam), 1716 (CO₂R), 1706 and 1510 (NHCO₂R) and 1590 and 1495 cm.⁻¹ (CONH), τ (CDCl₃) 2.63 (Ph), 3.07 (CONH, d, J 9 Hz), 4.19 (C₍₇₎-H, dd, J 4.5 and 9 Hz.), 4.29 (NHCH, d, J 7 Hz.), 4.78 (NHCH, d, J 7 Hz.), 5.11 (C₍₆₎-H, d, J 4.5 Hz.), 5.59 (CH₂C L, s), 6.42 and 6.69 (C₍₂₎-CH₂, AB-q, J_{AB} 18 Hz.), and 8.44 and 8.59 (t Butyls) (Found: C, 56.2; H, 6.2; N, 7.7. C₂₅H₃₂ClN₃O₆S requires C, 55.8; H, 6.0; N, 7.8%).

b.
[7β-(D-2-t-Butoxycarbonylamino-2-phenylacetamido)-4-t-butoxycarbonylceph-3-em-3-ylmethyl]triphenylphosphonium iodide A solution of t-butyl 7β-(D-2-t-butoxycarbonylamino-2-phenylacetamido)-3-chloromethylceph-3-em-4-carboxylate (2.5 g.) in acetone (20 ml.) was treated with a solution of sodium iodide (2.43 g., ca. 4 equiv.) in acetone (20 ml.). The mixture was stored in the dark for 2 hours, then poured into brine and the insoluble material extracted into ethyl acetate. The organic phase was washed with water and dilute aqueous sodium thiosulphite solution, and with further amounts of water, and dried and evaporated in vacuo. The residue, in ethyl acetate, was run into petroleum ether (b.p. 40 to 60°) to give the crude iodomethyl compound (2.48 g.) as an amorphous solid, m.p. 114° to 125° (decom.). [α] - 75.9° (CHCl₃), λ_{max}. 285 nm. (ε 7,550).

A solution of the iodomethyl derivative (1.55 g.) in ethyl acetate (10 ml.) was treated with a solution of triphenylphosphine (1.3 g.) in ethyl acetate (9 ml.) and the mixture stored in the dark for 1½ hours. The solution was run into petroleum ether (b.p. 40 to 60°) to give the phosphonium salt (1.8 g.) as an amorphous solid, m.p. 172 to 188° (decomp.), [α] - 2.4° (CHCl₃), λ_{max}. 269 nm. (ε 10,250) and 275.5 nm, (ε 9,900), ν_{max}. (CHBr₃) 3420 (NH), 1780 (β-lactam), 1700 and 1500 (CONH and NHCO₂R), and 1440 cm.⁻¹ (P-C aryl), τ (DMSO-d₆; spectrum not well resolved) 0.81 (NH, d, J ca. 9 Hz.), 2.13 (P-Ph), 2.61 (PhCH), 4.3 to 5.2 (NHCH,C₍₇₎-H, CH₂P, complex), and 8.6 and 8.79 (t.Butyl).

SECTION A (ii)

EXAMPLE 1

Diphenylmethyl 7β-(2-thienylacetamido)-3-(triphenylphosphoranylidene-methyl) ceph-3-em-4-carboxylate A solution of [4-diphenylmethoxycarbonyl-7β-(2-thienylacetamido) ceph-3-em-3-ylmethyl] triphenylphosphonium iodide (25 g.) in acetone (300 ml.) with water (40 ml.) was cooled to 0° and taken to pH 11 with 2N-sodium hydroxide. The mixture, containing a precipitated yellow solid, was diluted with acetone (200 ml.) and water (50 ml.), and filtered. The collected solid was washed with acetone and ether, and dried in vacuo to give diphenylmethyl 7β-(2-thienylacetamido)-3-(triphenylphosphoranylidenemethyl) ceph-3-em-4-carboxylate (17 g., 78.5%) as a yellow crystalline solid, m.p. 133°-138° (Decomp), [α]_D - 35° (CHCl₃), λ_{max} (CHCl₃) 388 nm. (ε 18,500), 273 nm (ε 6,240) and 267 nm (ε 6,940), ν_{max} (CHBr₃) 3360 (NH), 1746 (β-lactam), 1670 (CO₂R), 1642 and 1500 (CONH), and 1438 (P-C aryl) cm⁻¹; τ (CDCl₃) 4.82 (C₍₇₎-H, dd, J 4.5, 9Hz), 4.95 (C₍₆₎-H,d, J 4.5 Hz), 7.11 and 7.55 (C₍₂₎-CH₂, two dd. J_{H-H} 14 Hz., J_{P-H} 1-2 Hz) and 4.5

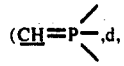

J_{P-H} 22 Hz). [Found: C 66.6; H, 4.7, N, 2.9; P, 3.9; S, 7.8. C₄₅H₃₇N₂O₄S₂P (764.8) requires C, 70.6; H, 4.8; N, 3.6; P, 4.0; S, 8.4%].

EXAMPLE 2

Diphenylmethyl 7β-(2-thienylacetamido)-3-(triphenylphosphoranylidene methyl) ceph-3-em-4-carboxylate A solution of [4-diphenylmethoxycarbonyl-7β-(2-thienylacetamido) ceph-3-em-3-ylmethyl] triphenylphosphonium bromide (26.4 mg.) in chloroform (5 ml.) was treated with ethoxycarbonylmethylenediphenylphosphorane (11 mg., ca 1 equiv.) in chloroform (5 ml.) and the solvent immediately removed in vacuo. The residue was treated with 10% aqueous acetone (5 ml.). The insoluble yellow crystalline material isolated by filtration and dried in vacuo to give the title compound (17 mg.), λ_{max} (CHCl₃) 388 nm (ε 19,200).

EXAMPLE 3.

Diphenylmethyl 7β-(2-Thienylacetamido)-3-(triphenylphosphoranylidenemethyl) ceph-3-em-4-carboxylate.

A solution of (4-diphenylmethoxycarbonyl-7β-(2-thienylacetamido)ceph-2-em-3-ylmethyl) triphenylphosphonium chloride (200 mg.) in acetone (6 ml.) was treated with saturated aqueous sodium bicarbonate solution (1 ml.) and water (1 ml.) and a few drops of 2N-aqueous sodium hydroxide. A yellow solid came out of solution. The mixture was diluted with water and filtered and the collected solid was washed with water and acetone and ether to give (after drying in vacuo) the ylid (135 mg., 70.5%) as a yellow crystalline solid, m.p. 198° to 199° (decomp.), [α] −67° (CHCl₃) (falling to −31° (CHCl₃) after 30 minutes at 23°), λ_{max}. (CHCl₃) 388 nm. (ε 20,100) and 266.5 nm. (ε 7.650). The ultraviolet, infrared and p.m.r. spectra were identical with those of sample described in Example A (ii) 1; there was no evidence for the presence of any Δ²-isomers.

SECTION A (iii)

EXAMPLE 1 a. Diphenylmethyl 7β-(2-thienylacetamido(-3-vinyl ceph-3-em-4-carboxylate.

A solution of diphenylmethyl 7β-(2-thienylacetamido)-3-(triphenylphosphoranylidenemethyl) ceph-3-em-4-carboxylate (2.55 g.) Rf 0.0, in methylene dichloride (150 ml.) was treated, at 10°, with 40% formaldehyde solution (20 ml.). The mixture was stirred vigorously at 10° until the orange colour characteristic of the starting material had disappeared (ca 30 minutes). The methylene chloride solution was dried and evaporated in vacuo. The residue was triturated with ethyl acetate and the insoluble crystalline material collected by filtration. The filtrate, on treatment with ether, gave a further crop of crystalline material. The combined solids (1.25 g., 72.5%) were crystallized from methanol to give pure diphenylmethyl 7β-(2-thienylacetamido)-3-vinylceph- 3-em-4-carboxylate (780 mg.), Rf 0.5, as small needles, m.p. 176 to 177° (dec) $[\alpha]_D$ 132.8°(CHCl$_3$), $\lambda_{max}$ 296 nm ($\epsilon$ 13,620) $\nu_{max}$ (CHBr$_3$) 3420 (NH), 1788 ($\beta$-lactam), 1720 (CO$_2$R), and 1680 and 1510 (CONH) cm$^{-1}$; $\tau$ (CDCl$_3$) 4.21 (C$_{(7)}$-H, dd, J 4.5 and 9 Hz), 5.06 (C$_{(6)}$-H, d, J 4.5 Hz), 6.36 and 6.58 (C$_{(2)}$-CH$_2$, AB-q, J$_{AB}$18 Hz), and 3.2 (dd), 4.65 (d) and 4.8 (d) (—CH = CH$_2$). ABX system, J$_{AX}$ 16 Hz., J$_{BX}$ 12 Hz., J$_{AB}$ 0Hz. [Found: C, 64.9; H, 4.8; N, 5.3; S, 12.4. C$_{28}$H$_{24}$N$_2$O$_4$S$_2$ (516.5) requires C, 65.1; H. 4.7; N, 5.4; S, 12.4%].

b. Diphenylmethyl 7β-amino-3-vinylceph-3-em-4-carboxylate

A suspension of phosphorus pentachloride (4.71 g., 22.5 mmole) in methylene dichloride (35 ml.) was warmed until most of the phosphorus pentachloride had dissolved. A solution of pyridine in methylene dichloride (18.2 ml., as a 10% v:v solution, ca 22.5 mmole pyridine) was added, and the white suspension was warmed to 23° for 10 minutes, then cooled to 0°. A solution of diphenylmethyl 7β-(2-thienylacetamido)-3-vinylceph-3-em-4-carboxylate (5.16 g., 10 mmole) in methylene dichloride (70 ml.), cooled to 0°, was added and the mixture stirred for 20 minutes. The solution was run into a vigorously stirred mixture of methanol (10 ml.) in methylene dichloride 50 ml.) and the resulting solution washed with aqueous sodium bicarbonate and water, and dried and evaporated in vacuo. The residual gum, in a small volume of chloroform, was run onto a column (7 × 4 cm.) of Kieselgel (0.02 to 0.5 mm.), and the column eluted with chloroform (2 × 100 ml.), then chloroform: ethyl acetate = 1:1 (3 × 100 ml.). The first chloroform fraction and the last chloroform : ethyl acetate fraction were discarded and the other fractions combined and evaporated in vacuo. The residue was triturated with ether to give the amine (2.7 g., 69%) as small needles, m.p. 157°–160° (decomp), $[\alpha]_D$ - 155.4° (CHCl$_3$9, $\lambda_{max}$. 296.5 nm. ($\epsilon$, 12,400), $\nu_{max}$. (CHBr$_3$) 3460 and 3390 (NH), 1780 ($\beta$-lactam), 1730 (CO$_2$R) and 910 cm.$^{-1}$ (CH=CH$_2$), $\tau$ (CDCl$_3$) 2.65 (Ph), 3.02 (CH Ph$_2$), 3.09 (CH=CH$_2$, dd, J 11 and 18 Hz.), 4.64 and 4.82 (CH=CH$_2$, two d, J 18 and 11 Hz. resp.), 5.09 (C$_{(7)}$-H, d, J 5 Hz.), 5.32 (C$_{(6)}$-H, d, J 5 Hz.), 6.35 and 6.85 (C$_{(2)}$-CH$_2$, Ab-q J 18 Hz), and 8.21 (NH$_2$); (DMSO-d$_6$) 2.60 (Ph), 3.03 (CH Ph$_2$), 3.28 (CH = CH$_2$, dd J 11 and 17 Hz.), 4.40 and 4.76 (CH=CH$_2$, two d, J 17 and 11 Hz. resp.), 4.91 (C$_{(7)}$-H, d, J 5 Hz.), 5.12 (C$_{(6)}$-H, d, J 5 Hz), 6.09 and 6.45 (C$_{(2)}$-CH$_2$, AB-q J 18 Hz.) and 7.62 (NH$_2$) (Found : C, 66.2; H, 5.1; N, 6.8; S, 8.1. C$_{22}$H$_{20}$N$_2$O$_3$S requires C, 67.3;, H, 5.15; N, 7.15; S, 8.2%).

c. Diphenylmethyl 7β-(D-2-t-butoxycarbonylamino-2-phenylacetamido)-3-vinylceph-3-em-4-carboxylate A solution of diphenylmethyl 7βamino-3-vinylceph-3-em-4-carboxylate (1.57 g., 4 mmole) in methylene dichloride (25 ml.) with dicyclohexylcarbodiimide (907 mg., 4.4 mmole) was treated slowly (over 10 minutes) with a solution of D-2-t-butoxycarbonylamino-2-phenylacetic acid (1.1 g., 4.4 mmole) in N,N-dimethylformamide (10 ml.). The mixture was stirred at 23° for 30 minutes and dicyclohexylurea removed by filtration. The filtrate was washed with water and dried and evaporated in vacuo to give a pale yellow solid. This material was crystallised from methanol, and the isolated material washed with ether, to give the crude title cpompound (2.2 g.) (contaminated with dicyclohexylurea). The crude compound in benzene :ethyl acetate (2:5) was filtered through a short column of Kieselgel 0.02 - 0.5 mm., 10 cm. × 2.5 cm.). Evaporation of the solvent in vacuo and washing the crystalline residue with ether gave the pure title compound (1.6 g., 64%) as small needles m.p. 200°–202°, $[\alpha]_D$ - 129° (CHCl$_3$), $\lambda_{max}$ 294.5 nm. ($\epsilon$ 14,400), $\nu_{max}$. 3395 (NH), 1780 ($\beta$-lactam), 1712 (CO$_2$R), 1690 and 1500 (CONH) and 912 cm.$^{-1}$ (CH=CH$_2$),$\tau$(CDCl$_3$) 3.05 (CHPh$_2$),3.03 (CH=CH$_2$, dd, J 17 and 11 Hz). 3.08 (NH, d, J 9 Hz) 4.23 (C$_{(7)}$-H, dd, J 9 and 4.5 Hz), 4.28 (CH-NH, d, J 7 Hz), 4.65 and 4.79 (CH=CH$_2$, two d, J 17 and 11 Hz resp.), 4.77 (CH-NH, d, J 7 Hz), 5.10 (C$_{(6)}$-H, d, J 4.5 Hz), 6.46 and 6.70 (C$_{(2)}$-CH, AB-q, J 18 Hz) 8.58 (C[CH$_3$]$_3$). (Found: C, 66.6; H, 5.6; N, 6.4; S, 5.1. C$_{35}$H$_{35}$N$_3$O$_6$S requires C, 67.2; H, 5.65; N, 6.7; S, 5.1%).

d. 7β-(D-2-Amino-2-phenylacetamido)-3-vinylceph-3-em-4-carboxylic acid

A solution of diphenylmethyl 7β-(D-2-t-butoxycarbonylamino-2-phenylacetamido)-3-vinylceph-3-em-4-carboxylate (1.4 g.) in anisole (1.4 ml.) was treated, at 23°, with trifluoroacetic acid (5.6 ml.). After 4 minutes the solvents were removed in vacuo and the residue partitioned between ethyl acetate and water containing trifluoroacetic acid (ca 0.25 ml.). The aqueous phase was separated and the ethyl acetate washed thoroughly with more dilute aqueous trifluoroacetic acid (6 × 30 ml.). Traces of ethyl acetate were removed from the aqueous solution in vacuo and after ca 30 minutes at room temperature material (221 mg.) which had crystallised out was isolated by filtration. The aqueous solution was freeze dried and the residue taken up in a small volume of water (ca 20 ml.) and a second crop (350 mg.) of crystalline material was isolated by filtration. The crystalline material was combined to give the title compound (571 mg.) as small prisms m.p. 190° (decomp.), $[\alpha]_D$ - 96.2° (5% NaHCO$_3$), $\lambda_{max}$. (0.2 m pH 7 phosphate buffer) 287.5 nm. ($\epsilon$ 11,360), $\lambda_{max}$. ca 3540 (H$_2$O), 2600 (NH$_3$), 1750 ($\beta$-lactam), 1690 and 1530 (—CONH—), 1570 (—CO$_2$) and 920 cm.$^{-1}$ (C=CH$_2$), $\tau$ (CF$_3$CO$_2$H) 2.2 (-N$^+$H$_3$), 2.42 (phenyl), 2.63 (CH=CH$_2$, dd, J 17 and 11 Hz), 4.22 (C$_{(7)}$-H, partially obscured dd), 4.24 and 4.36 (CH=CH$_2$, two d, J 17 and 11 resp.), 4.46 (CH-NH$_3$, ill resolved q), 4.78 (C$_{(6)}$-H, d, J 4.5 Hz) and 6.37 (C$_{(2)}$-CH$_2$), (Found: C 51.7; H, 5.2; N, 11.0; S, 8.1. C$_{17}$H$_{17}$N$_3$O$_4$S. 2H$_2$o requires C, 51.6; H, 5.35; N, 10.65; S, 8.1%). Rf. 0.15 (System B)

EXAMPLE 2 a. t-Butyl 7β-Phenoxyacetamide-3-vinylceph-3-em-4-carboxylate

A solution of t-butyl 3-bromomethyl-7β-phenoxyacetamidoceph-3-em-4-carboxylate, 1β-oxide (24.97 g, 50.5 mmole) and triphenylphosphine (16.4 g, 1.25 equiv.) in dry methylene chloride (300 ml) was stirred at ca. 20° for 16 hours and then cooled to −20°. A solution of phosphorus tribromide (7.34 ml, 1.5 equiv.) in dry methylene chloride (100 ml) was added with stirring over a period of 30 minutes with the reaction temperature being maintained at −20°; the mixture was then stirred at this temperature for a further hour. 40%-Formaldehyde solution (190 ml) and saturated aqueous sodium hydrogen carbonate solution (750 ml) were added in one portion, and the two-phase mixture was stirred vigorously while its temperature was allowed to reach 20° and then held at this temperature for a further hour. The organic phase was washed with water, dried (MgSO$_4$), and evaporated, and the residue was chromatographed on Kieselgel G (Merck, 0.05 to 0.2 mm, 800 g), eluting with benzene-ethyl acetate (15:1) and (10:1) (2 liters of each). Appropriate fractions were combined and evaporated to give the title ester as a pale-yellow foam (13.53 g, 63%), [α]$_D$ - 44° (C 1.00; Me$_2$SO), λ$_{max}$ (EtOH) 292.5 nm (ε 15,300), inflexions at 269.5 and 276.5 nm (ε 10,000 and 12,400), having a p.m.r. spectrum (Me$_2$SO-d$_6$) appropriate to its structure.

b. t-Butyl 7β-Amino-3-vinylceph-3-em-4-carboxylate Hydrogen p-Toluene-sulphonate A solution of t-butyl 7β-phenoxyacetamido-3-vinyl-ceph-3-em-4-carboxylate (833 mg, 2 mmole) in dry methylene chloride (10 ml) was maintained at 0° while dry pyridine (237 mg, 1.5 equiv.) and phosphorus pentachloride (625 mg) were added. The suspension was allowed to warm to 23° over a period of 15 minutes (by which time all the solid had dissolved) and then stirred at this temperature for 1¾ hours. The orange solution was added dropwise to stirred, dry methanol (5 ml) previously cooled to −20°; the temperature of the methanol solution was kept at ca. −20° throughout the addition. The solvents were removed in vacuo and the residual oil was partitioned between water (5 ml) and ethyl acetate (10 ml.) The aqueous phase was washed with ethyl acetate (5 ml) and the combined organic phases were back-washed with 0.5 N-hydrochloric acid (5 ml). The aqueous phase and acid washings were combined and treated with a solution of p-toluenesulphonic acid monohydrate (380 mg, 2 mmole) in water (2 ml), when refrigeration at 5° for 30 minutes failed to give any solid. Ethyl acetate (5 ml) was added and the pH of the mixture was adjusted to 4.9 with 2N-sodium hydroxide solution. The aqueous phase was re-extracted with ethyl acetate (5 ml). and the combined ethyl acetate extract was washed with water (10 ml), dried (MgSO$_4$) and evaporated to low volume. Addition of a solution of p-toluenesulphonic acid monohydrate (380 mg, 2 mmole) in ethyl acetate (15 ml) caused the separation of a white solid. The mixture was refrigerated for 1 hour when the solid was filtered off, washed with ethyl acetate and dried to give the *title p-toluenesulphonate* (467 mg, 51%), m.p. > 200°, [α]$_D^{22}$ - 80° (C 1.03; MeOH), λ$_{max}$ (MeOH) 293.5 nm (ε 14,350). Crystallisation from warm ethanol-ether gave a feathery solid, [α]$_D^{23}$ - 82° (C 1.01; MeOH), λ$_{max}$ (MeOH) 222 and 295 to 296 nm (ε 15,700 and 15,300), ν$_{max}$ (Nujol) ca., 2600 (NH$_3^+$), 1770 (azetidin-2-one), 1716 (CO$_2$R), 1142 (SO$_3^-$) and 906 cm$^{-1}$ (=CH$_2$), τ (Me$_2$SO-d$_6$) 2.45 (2H, d, J 8 Hz; C$\underline{H}$=C-SO$_3^-$), 2.84 (2H, d, J 8 Hz; C$\underline{H}$=C-CH$_3$), 3.11 (1H, dd, J 11.5 and 17.5 Hz; C$\underline{H}$=CH$_2$), 4.28 (1H, d, J17.5 Hz) and 4.58 (1H, d, J 11.5 Hz) (CH=C$\underline{H}_2$), 4.69 and 4.78 (1H and 1H, 2 d, J 5 Hz; C$_7$-$\underline{H}$ and C$_6$-$\underline{H}$), 6.01 and 6.33 (2H, AB-q, J 18 Hz; C$_2$-H$_2$), 6.71 (3H, s; C$\underline{H}_3$C$_6$H$_4$), 8.51 (9H, s; CO$_2$C(CH$_3$)$_3$) (Found: C, 52.3, 52.5; H, 5.9, 5.9; N, 5.8, 6.1; S, 14.2. C$_{20}$H$_{26}$N$_2$O$_6$S$_2$ (454.6) requires C, 52.8; H, 5.8; N, 6.2, S, 14.1%).

c. ACYLATION OF t-BUTYL 7β-AMINO-3-VINYLCEPH-3-EM-4-CARBOXYLATE with p-Nitrophenylacetic Acid A suspension of t-butyl 7β-amino-3-vinylceph-3-em-4-carboxylate hydrogen p-toluenesulphonate (1.14 g, 2.5 mmole) in methylene chloride (25 ml) was shaken with 4 percent aqueous sodium hydrogen carbonate solution (10 ml) until the organic phase cleared. The aqueous phase was re-extracted with methylene chloride (10 ml), and the combined organic phases were washed with water (10 ml) and dried (MgSO$_4$). The solution of t-butyl 7β-amino-3-vinylceph-3-em-4-carboxylate so obtained was stirred and treated with a solution of dicyclohexylcarbodiimide (515 mg, 1 equiv.) in dry methylene chloride (10 ml). A solution of p-nitrophenylacetic acid (453 mg, 1 equiv.) in methylene chloride (15 ml) was added over a period of 5 minutes and the mixture was stirred at 30° for 2 hours. The precipitated N,N'-dicyclohexylurea was filtered off, and the filtrate was washed with 3%-sodium hydrogen carbonate solution (50 ml), water (50 ml), 2N-hydrochloric acid (25 ml) and water (25 ml), dried (MgSO$_4$) and evaporated to an orange gelatinous solid. This solid was triturated with ethyl acetate (150 ml), the insoluble dicyclohexylurea was removed by filtration, and the filtrate was evaporated to give t-butyl 7β-(p-nitrophenylacetamido)-3-vinylceph-3-em-4-carboxylate (1.02 g, 92%) (see Table 1)

Similar acylations to that described above were carried out with i. D(−)-α-Formyloxy-α-phenylacetic Acid ii. D(−)-α-Dichloroacetoxy-α-phenylacetic Acid and these examples are summarised in Table 1. The infrared spectra (in bromoform) and p.m.r. spectra (in deuterochloroform) of the products of Example 13b(i) and (ii) were consistent with their being the appropriate t-butyl 7β-acylamido-3-vinylceph-3-em-4-carboxylate esters containing 5 to 20% by weight of N,N'-dicyclohexylurea and/or the appropriate N-acyl-N,N'-dicyclohexylurea.

Notes to Table 1

Δ NaHCO$_3$ wash replaced by wash with 0.2M pH 7 phosphate buffer (50 ml)

≠ NaHCO$_3$ and 2N-HCl washes both omitted.

Table 1

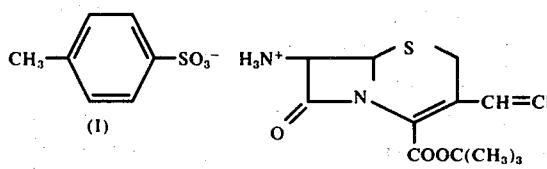

↓ NaHCO₃

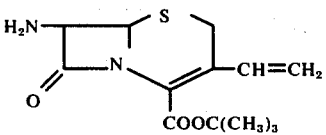

↓ RCOOH
Dicyclohexylcarbodiimide

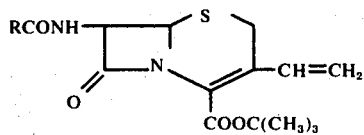
(II)

| Example | R. | Mmole of (I) and RCO₂H | % Wt. Yield of (II) | $\lambda_{max}$ nm | $E^{1\%}_{1cm}$ |
|---|---|---|---|---|---|
| 2c (i) | D-α-formyloxybenzyl Δ | 1 | 92 | 293.5 | 284 |
| 2c (ii) | D-α-dichloroacetoxy benzyl | 2.66 | 103 | 293.5 | 233 |

EXAMPLE 2c (ix) cont t-Butyl 7β-(D-α-Hydroxy-α-phenylacetamido)-3-vinylceph-3-em-4-carboxylate

A solution of t-butyl 7β-(D-α-dichloroacetoxy-α-phenylacetamido)-3-vinylceph-3-em-4-carboxylate (1.42 g., 2.7 mmole) in methylene chloride (30 ml.) was stirred vigorously for 5 hours with 4% aqueous sodium hydrogen carbonate solution (30 ml.). The organic phase was washed with water (25 ml), dried (MgSO₄) and evaporated to an orange foam which was chromatographed on Kieselgel G (Merck, 0.05 to 0.2 mm; 50 g) with benzene-ethyl acetate (19:1; 300 ml.) and (9:1; 200 ml.) as eluant. The appropriate fractions were combined and evaporated to give the title ester as a pale-orange crystalline solid (485 mg., 43%), $\lambda_{max.}$ (EtOH) 294 nm (ε 13,750), τ (CDCl₃) 2.62 (5H, s; C₆H₅), 2.86 (1H, d, J 9 Hz; NH); 2.94 (1H, dd, J 11 and 18 Hz; CH=CH₂), 4.25 (1H, dd, J 9 and 5 Hz; C₇-H), 4.59 (1H, d, J 18 Hz) and 4.70 (1H, J 11 Hz) (CH=CH₂), 4.87 (1H, s; CHOH), 5.04 (1H, d, 5 Hz; C₆-H), 6.35 and 6.59 (2H, AB-q, J 18 Hz; C₂-H₂), 8.47 (9H, s; CO₂C(CH₃)₃).

d. DE-ESTERIFICATION OF t-BUTYL 7β-ACYLAMIDO-3-VINYLCEPH-3-EM-4-CARBOXYLATE ESTERS

The t-butyl esters listed below were treated with trifluoroacetic acid and anisole as in Example A(iii) 11(b) to give the corresponding 7β-acylamido-3-vinylceph-3-em-4-carboxylic acids. The physical properties of the products are summarised in Tables 2,3 and 4. (1) t-Butyl 7β-(D-2-Formyloxy-2-phenylacetamido)-3-vinylceph-3-em-4-carboxylate (Example 2 (c) (i) cont). (2) t-Butyl 7β-(D-2-Hydroxy-2-phenylacetamido)-3-vinylceph-3-em-4-carboxylate (Example 2 (c) (ii) cont).

Table 2

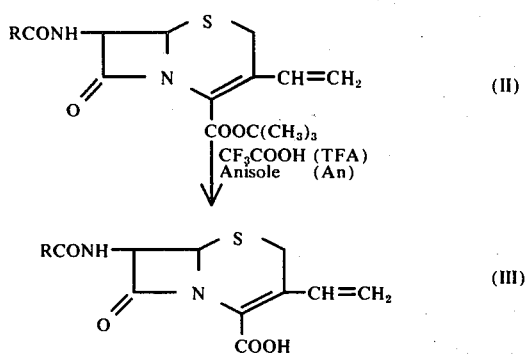

In Example 2 (d) (1) R is D-α-formyloxybenzyl
(2) R is D-α-hydroxybenzyl

| Example | M mole of II | ml of TFA an | % Yield of cryst. III | M.p. | λ_max nm(ε) | [α]_D | R_p (system C) |
|---|---|---|---|---|---|---|---|
| 2(d) (1) | 2.52 | 12 3 | 61 | 124–129° | 291(11,900) | −46.7° | 1.76* |
| 2(d) (2) | 1.10 | 5 1 | 77 | — | 290(11,300) | −60.8° | 0.84 |

*With streaking from R_p 1.76 to R_p 0.84

Table 3

Infrared spectra of

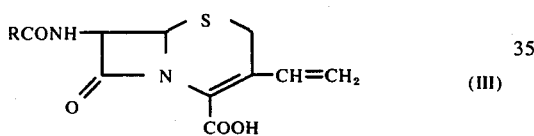

as Nujol mulls quoted in cm$^{-1}$

| Example | NH | azetidin-2-one | CO_2H | CONH | R |
|---|---|---|---|---|---|
| 2(d) (1) | 3315 | 1778 | 1710 | 1680 and 1540 | 1728 (OCHO) |
| 2(d) (2) | ca. 3300 | 1760 | 1695 | 1695 and 1505 | |

Table 4

P.m.r. spectra in Me_2SO-d_6 solution of

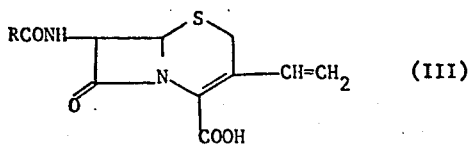

quoted as τ values (coupling constants (J) in Hz shown in brackets)

| Example | | CH=CH_2 dd | CH=CH_2 2 doublets | |
|---|---|---|---|---|
| 2(d) | (1) | 3.08 (11 and 18) | 4.38(18), | 4.70 (11) |
| 2(d) | (2) | 3.04 | 4.40(18), | 4.67 |
| | | (11 and 18) | | (11) |

EXAMPLE 3 a. DL-2-Amino-2-(2-naphthyl)acetic acid

A solution of 5-(2-naphthyl) hydantoin (10g., 44.5 mmole) in 10% sodium hydroxide solution (50 ml.) was heated under reflux for 18 hours. The solution was cooled, filtered, diluted and treated with concentrated hydrochloric acid to bring the pH to 5.0. The resulting solid was filtered off washed with water and added to 5N-hydrochloric acid (2 L). Insoluble material was filtered off and the filtrate was taken to pH 5.0 with 40% sodium hydroxide solution. On standing, the amino-acid crystallised out as platelets (3.92 g.) m.p. 238°–240°, λλ_max. (pH 6.0 phosphate) 225 ε 51,700), 276 (ε 3,520), 268 nm. (ε 3,420).

b. DL-2-t-Butoxycarbonylamino-2-(2-naphthyl) acetic acid

2N- Sodium hydroxide (12.6 ml.) was added to suspension of DL-2-amino-2-(2-naphthyl) acetic acid (5.06 g., 25.2 mmole) in a solution of sodium carbonate (7.93 g., 75.6 mmole) in water (25 ml.). t-Butanol (36 ml.) was then added and the mixture heated under reflux to obtain a clear solution. t-Butyl p-nitro-phenyl-carbonate (12.1 g., 50.4 mmole) was then added in portions during 3 hours and the mixture was heated for a further hour. t-Butanol was removed in vacuo and the yellow solid was filtered off. The filtrate was covered with isopropyl ether and the pH was adjusted to 5.0 by the addition of concentrated hydrochloric acid. The layers were separated and the aqueous layer extracted again with isopropyl ether. The combined ethereal extracts were extracted three times with saturated sodium bicarbonate solution and the combined aqueous extracts were acidified with concentrated hydrochloric acid and extracted with ethyl acetate. The organic extract was washed with water and brine, dried over magnesium sulphate, and concentrated in vacuo to give a solid that was triturated with petroleum (40°–60°) to afford the protected amino-acid as a pink solid (4.04 g.) m.p. 149° (decomp.), $\lambda\lambda_{max}$. (ethanol) 226 ($\epsilon$ 69,500), 268 ($\epsilon$ 4,720), 275 nm. ($\epsilon$ 5,100).

c. t-Butyl 7β-[DL-2-t-Butoxycarbonylamino-2-(2-naphthyl)-acetamido]-3-vinylceph-3-em-4-carboxylate.

A suspension of t-butyl 7β-amino-3-vinylceph-3-em-4-carboxylate hydrogen p-toluenesulphonate (1.14 g. 2.5 mmole) in methylene chloride was shaken with a solution of sodium hydrogen carbonate (206 mg., 1 equiv.) in water (20 ml.) until the organic layer cleared. The aqueous phase was re-extracted with methylene chloride (20 ml.), and the combined organic phases were washed with water (20 ml.), and dried. The solution of t-butyl 7β-amino-3-vinylceph-3-em-4-carboxylate so obtained was stirred and treated with a solution of DL-dicyclohexylcarbodiimide (515 mg., 1 equiv.) in methylene chloride (20 ml.), followed by a solution of Dl-2-t-butoxycarbonylamino-2-(2-naphthyl) acetic acid (753 mg., 1.0 equiv.) in methylene chloride (20 ml.), previously warmed to achieve solution. The reaction mixture was stirred at 23° for 2½ hours, and the precipitated N,N'-dicyclohexylurea was filtered off. The filtrate was washed with 3%-sodium hydrogen carbonate solution (30 ml.), water (20 ml.), 2N-hydrochloric acid (20 ml.), and water (20 ml.), dried and evaporated to a pale-yellow solid. This solid was triturated with ethyl acetate (160 ml.), the insoluble dicyclohexylurea was removed by filtration, and the filtrate was evaporated to give the title ester as a crystalline solid (1.26 g, 80%), $\lambda_{max}$. 288 nm ($E_{1cm}^{1\%}$ 283), $\lambda_{max}$. (CHBr$_3$) 3426 (NH), 1780 (azetidin-2-one), 1720 (CO$_2$R), 1708 and 1500 (NH CO$_2$R), 1694 (CONH) and 908 cm$^{-1}$ (=CH$_2$). The pmr spectrum of the product in CDCl$_3$ showed it to be a 1:1-mixture of the two diastereoisomers (the new centre of asymmetry is in the side-chain attached to the 7-position). d. 7β-[DL-2-Amino-2(2-naphthyl)acetamido]-3-vinylceph-3-em-4-carboxylic Acid A solution of t-butyl 7β-(DL-2-t-butoxycarbonylamino-2-[2-naphthyl]acetamido)-3-vinylceph-3-em-4-carboxylate (1.24 g. 2.19 mmole) in trifluoroacetic acid (16 ml.) and anisole (5 ml.) was kept at 24° for 10 minutes. The solvents were removed in vacuo to give an orange solid which was triturated and then stirred for 30 minutes with a mixture of ether (20 ml.) and ethyl acetate (5 ml.). The supernatant liquors were decanted and the procedure was repeated with a similar ethyl acetate-ether mixture. The off-white crystalline solid so obtained was filtered off, washed with ethyl acetate-ether (1:4) and dried to give a ca. 1:1-mixture of the hydrated title amino-acid and its trifluoroacetate salt (0.82 g, 77.5%) m.p. 190° to 195°, [α] −55.4°, $\lambda_{max}$. (dissolved in one drop of N,N-dimethylformamide and diluted with ethanol) 280.5 ($\epsilon$ 16,700) and 288 nm ($\epsilon$ 17,300), $\lambda_{max}$. 3500 (H$_2$O), 2600 (NH$_3$ and CO$_2$H), 1770 (azetidin-2-one), 1680 (CF$_3$CO$_2$) and 900 cm$^{-1}$ (=CH$_2$) (Found: C, 54.6, 54.5; H, 4.4, 4.4; F, 5.8; N, 8.4, 8.1; S, 6.25. C$_{21}$H$_{19}$N$_3$O$_4$S. 0.5 CF$_3$CO$_2$H. H$_2$O (484.5) requires C, 54.6; H, 4.5; F, 5.9; N, 8.7; S, 6.6%), Rp (system A) 0.31. The pmr spectrum of the product in Me$_2$SO-d$_6$ showed it to be a 1:1-mixture of the two diastereoisomers.

Biological results of certain of the compounds prepared in the Examples are given in Table V below.

Table V

| | Tube Dilution Assay (γ/ml.) | | | | | | | |
|---|---|---|---|---|---|---|---|---|
| | Gram Positive | | | | | Gram Negative | | |
| Compound | Staph. aureus 604 | Staph. aureus 663 | Staph. aureus 3452 | Staph. aureus 11127 | Strep. faecalis 850 | E. coli 573 | S. typh 804 | Pr. mirab 431 |
| "2d 1 | 1.6 | 0.2 | 1.6 | 6.2 | | 62 | 31 | 8 |
| "2d 2 | 1.6 | 0.2 | 1.6 | 6.2 | | 31 | 31 | 16 |
| "3(d) | 2.5 | 0.6 | 2 | 2 | | >250 | 250 | 250 |

Pharmaceutical Examples

A. Tablet

| | | |
|---|---|---|
| a) | 7-(D-2-Amino-2-phenylacetamido)-3-vinylceph-3-em-4-carboxylic acid | 250 mg. |
| b) | Mannitol | 75 mg. |
| c) | Potato Starch | 46 mg. |
| d) | Maize Starch | 25 mg. |
| e) | Magnesium stearate | 4 mg. |

The dry ingredients (a), (b) and (c) were blended together and granulated with a 10% aqueous paste of (d). The granules were passed through a No. 12 mesh (B.S.) screen dried to constant weight and sieved through a No. 16 mesh (B.S.) screen. The granules were then lubricated by blending in (e) and compressed at 400 mg. per tablet on suitable punches. The tablets may be coated if required, for instance with a readily soluble conventional film coating.

B. Capsule

| | |
|---|---|
| 7-(D-2-Amino-2-phenylacetamido)-3-vinylceph-3-em-4-carboxylic acid | 250 mg. |
| *Aerosil compositum | 3 mg. |

*A silicon dioxide/starch blend available from Bush, Beach and Gent of Marlon House, Lloyd's Avenue, London, B.C.3

The dry powders were blended together homogeneously and distributed into well filled, hard gelatine capsules, so that each contained 250 mg. of the active ingredient.

I claim:
1. A compound of the formula:

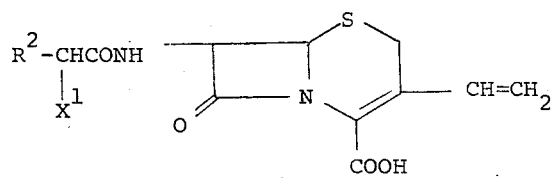

wherein $R^2$ is phenyl; phenyl mono substituted with halo, hydroxy, lower alkyl, nitro, amino, lower alkanoyl, lower alkoxy or lower alkylmercapto; thien-2-yl; thien-3-yl; or napthyl, $X^1$ is amino, hydroxyl, or formyloxy or a physiologically acceptable base or acid addition salt thereof.

2. The compound of claim 1 which is 7β-(D-2-amino-2-phenylacetamido)-3-vinylceph-3-em-4-carboxylic acid.

3. The compound of claim 1 which is 7β-[DL-2-amino-2-(2-naphthyl) acetamido]-3-vinylceph-3-em-4-carboxylic acid.

4. The compound of claim 1 which is 7β-(D-2-formyloxy-2-phenylacetamido)-3-vinylceph-3-em-4-carboxylic acid.

5. The compound of claim 1 which is 7β-(D-2-hydroxy-2-phenylacetamido)-3-vinylceph-3-em-4-carboxylic acid.

* * * * *